United States Patent
Meunier et al.

(10) Patent No.: US 11,939,409 B2
(45) Date of Patent: Mar. 26, 2024

(54) CROSS-LINKED POLYCARBOXYLATED POLYSACCHARIDES AND METHODS OF USE THEREOF

(71) Applicant: HALLURA LTD., Yokneam (IL)

(72) Inventors: Stephane Meunier, Herzliya (IL); Svetlana Shneider, Haifa (IL); Elena Ragozin, Ashqelon (IL)

(73) Assignee: HALLURA LTD., Yokneam (IL)

( * ) Notice: Subject to any disclaimer, the term of this patent is extended or adjusted under 35 U.S.C. 154(b) by 305 days.

(21) Appl. No.: 17/256,182

(22) PCT Filed: Jun. 11, 2019

(86) PCT No.: PCT/IL2019/050663
§ 371 (c)(1),
(2) Date: Dec. 25, 2020

(87) PCT Pub. No.: WO2020/003298
PCT Pub. Date: Jan. 2, 2020

(65) Prior Publication Data
US 2021/0261693 A1    Aug. 26, 2021

Related U.S. Application Data

(60) Provisional application No. 62/691,035, filed on Jun. 28, 2018.

(51) Int. Cl.
| | | |
|---|---|---|
| *C08B 37/08* | (2006.01) | |
| *A61L 27/20* | (2006.01) | |
| *A61L 27/52* | (2006.01) | |
| *C07D 237/26* | (2006.01) | |
| *C07D 257/08* | (2006.01) | |

(52) U.S. Cl.
CPC .......... *C08B 37/0072* (2013.01); *A61L 27/20* (2013.01); *A61L 27/52* (2013.01); *C07D 237/26* (2013.01); *C07D 257/08* (2013.01); *A61L 2300/402* (2013.01); *A61L 2300/428* (2013.01); *A61L 2400/06* (2013.01)

(58) Field of Classification Search
CPC ............................ C08B 37/0072; A61L 27/20
See application file for complete search history.

(56) References Cited

U.S. PATENT DOCUMENTS

2017/0189581 A1    7/2017    Desai et al.

FOREIGN PATENT DOCUMENTS

| WO | 2015154078 A1 | 10/2015 |
|---|---|---|
| WO | 2016209062 A1 | 12/2016 |
| WO | 2017075055 A1 | 5/2017 |
| WO | 2017210484 A1 | 12/2017 |

OTHER PUBLICATIONS

Bulpitt, Paul et al., Journal of Biomedical Materials Research, 1999, vol. 47, No. 2, pp. 152-169 (Year: 1999).*
Kablik, Jeffrey et al., Dermatologic Surgery, 2009, vol. 35, pp. 302-312 (Year: 2009).*
Famili, Amin et al., "Bio-Orthogonal Cross-Linking Chemistry Enables In Situ Protein Encapsulation and Provides Sustained Release from Hyaluronic Acid Based Hydrogels", Molecular Pharmaceutics, 14, 2017, pp. 1961-1968.
Zhang, Han et al., "Interfacial Bioorthogonal Cross-Linking", ACS Macro Letters, Mar. 2014, pp. 727-731.
Dicker, Kevin T. et al., "Patterned liquid-filled hydrogel channels formed via tetrazine ligation for in vitro vasculature models", Abstracts of Papers, 254th ACS National Meeting & Exposition, Washington, DC, USA, Aug. 20-24, 2017.
Jia, Xinqiao, "Diffusion-controlled interfacial bioorthogonal polymerization", Abstracts of Papers, 251st ACS National Meeting & Exposition, San Diego, CA, United States, Mar. 13-17, 2016.
Dicker, Kevin T. et al., "Interfacial bioorthogonal crosslinking for the fabrication and patterning of functional hydrogels", Abstracts of Papers, 250th ACS National Meeting & Exposition, Boston, MA, United States, Aug. 16-20, 2015.
Dicker, Kevin T. et al., "Interfacial bioorthogonal crosslinking for the fabrication of functional hydrogels", Abstracts of Papers, 248th ACS National Meeting & Exposition, San Francisco, CA, United States, Aug. 10-14, 2014.
Sébastien Pierre et al., "Basics of Dermal Filler Rheology" American Society for Dermatologic Surgery, Inc., 2015, 41:S120-S126; DOI: 10.1097/DSS.0000000000000334.
Dicker et al., "Core-shell patterning of synthetic hydrogels via interfacial bioorthogonal chemistry for spatial control of stem cell behavior" Chemical Science Sep. 2018, pp. 5394-5404. DOI:10.1039/C8SC00495A.

* cited by examiner

*Primary Examiner* — Bahar Craigo
(74) *Attorney, Agent, or Firm* — The Roy Gross Law Firm, LLC; Roy Gross

(57) ABSTRACT

The present invention is directed to a polymer comprising a first hyaluronic acid (HA) chain and a second HA chain crosslinked via a linker comprising an unsaturated moiety or a derivative thereof coupled to a tetrazine moiety or a derivative thereof. In some embodiments, the polymer of the invention is characterized by having a crosslinking degree of 0.2 to 4%.

15 Claims, 5 Drawing Sheets

CROSS-LINKED POLYCARBOXYLATED POLYSACCHARIDES AND METHODS OF USE THEREOF

CROSS REFERENCE TO RELATED APPLICATIONS

This application is a National Phase of PCT Patent Application No. PCT/IL2019/050663 having International filing date of Jun. 11, 2019 which claims the benefit of priority under 35 U.S.C. § 119(e) of U.S. Provisional Patent Application No. 62/691,035, filed Jun. 28, 2018 entitled "CROSS-LINKED POLYCARBOXYLATED POLYSACCHARIDES AND METHODS OF USE THEREOF." The contents of the above applications are all incorporated by reference as if fully set forth herein in their entirety.

FIELD OF INVENTION

The present invention, in some embodiments thereof, relates to cross-linked hyaluronic acid.

BACKGROUND OF THE INVENTION

Crosslinking of hyaluronic acid in dermal fillers confers the desired mechanical properties and in particular the lifting (or volumizing) properties of the material.

The desire to use a material as close as possible to the endogenous hyaluronic acid, dictates the production of material having low degrees of modification (e.g., % cross-linking). Both hyaluronic acid and crosslinked hyaluronic acids are known to be highly hygroscopic. Therefore, when these materials are injected, they have tendency to attract water in the tissue and lead to swelling and edema. Water attraction positively correlates with the content of hyaluronic acid and crosslinked hyaluronic acid. Accordingly, due to the need to reduce the risk of swelling and edema it is desirable to produce dermal fillers with low content in hyaluronic acid and crosslinked hyaluronic.

Current materials on the market are known to comprise either high crosslinking degrees (4 to 10%) or total hyaluronic acid content (equal or greater than 20 mg/gr) in order to provide sufficient lifting properties.

SUMMARY OF THE INVENTION

The present invention, in some embodiments thereof, relates to a cross-linked hyaluronic acid.

In one aspect of the invention, there is provided a polymer comprising a first hyaluronic acid (HA) chain and a second HA chain crosslinked via a linker comprising an unsaturated moiety or a derivative thereof bound to a tetrazine moiety or a derivative thereof, and wherein crosslinking is characterized by a crosslinking degree of 0.2 to 4%.

In some embodiments, the unsaturated moiety comprises: an unsaturated cycloalkyl, an unsaturated alkaryl, an unsaturated alkyl or a combination thereof.

In some embodiments, one or more linkers comprise a compound represented by formula (A):

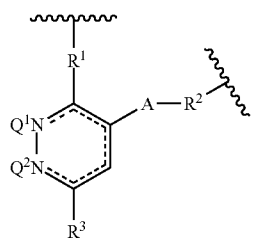

or by formula (B):

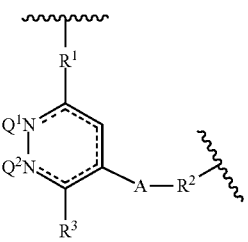

or a combination thereof; wherein:
- - - - represents a single or a double bond;
- $R^1$, $R^2$, or both, are selected from the group consisting of: a bond, alkyl, alkenyl, cycloalkyl, aryl, heteroaryl, heteroalicyclic, C(O)—NH-alkyl-NH, and alkyl-NZ, wherein Z is a bond, aryl, or heteroaryl;
- A is selected form the group consisting of: a bond, alkyl, and aryl;
- $Q^1$, $Q^2$ or both represent hydrogen, or are absent;
- and wherein R3 is selected from the group consisting of: hydrogen, alkyl, aryl, and heteroaryl substituted or non-substituted.

In some embodiments, the unsaturated moiety comprises a styrene moiety, or a derivative thereof.

In some embodiments, styrene moiety or a derivative thereof is represented by formula IA-D:

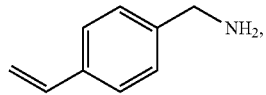

IA

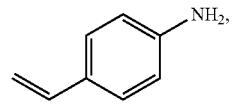

IB

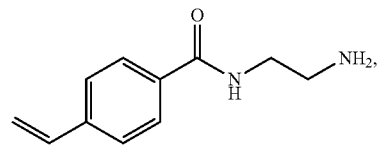

IC

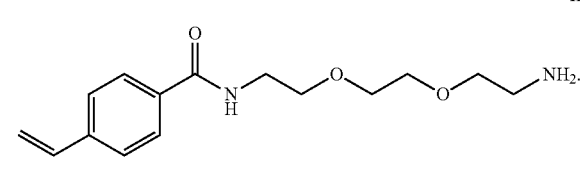

ID

In some embodiments, one or more linkers comprise a compound represented by formula (C):

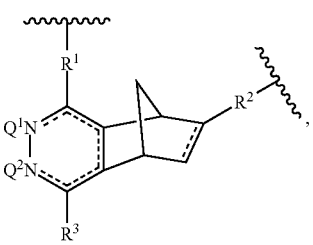

or by formula (D):

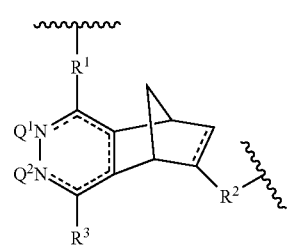

or a combination thereof; wherein:
- - - represents a single or a double bond;
$R^1$, $R^2$, or both, are selected from the group consisting of: a bond, alkyl, alkenyl, cycloalkyl, aryl, heteroaryl, heteroalicyclic, C(O)—NH-alkyl-NH, and alkyl-NZ, wherein Z is a bond, aryl, or heteroaryl;
$Q^1$, $Q^2$ or both represent hydrogen, or are absent;
and wherein $R^3$ is selected from the group consisting of: hydrogen, alkyl, aryl, and heteroaryl substituted or non-substituted.

In some embodiments, one or more linkers comprise:
a) a first compound derived from a norbornene moiety selected from formulae IIA-G:

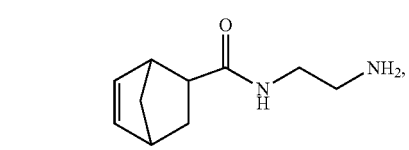
IIA

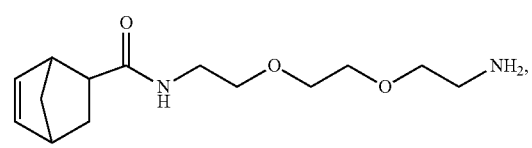
IIB

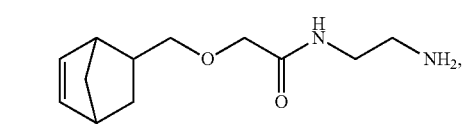
IIC

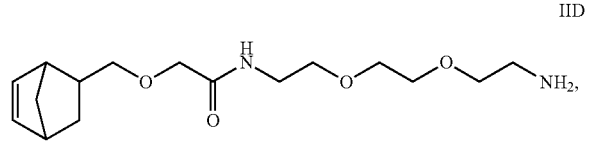
IID

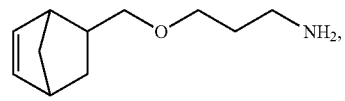
IIE

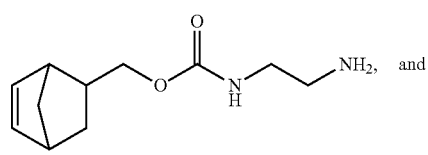
IIF and

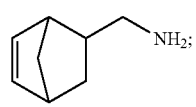
IIG and
b) a second compound derived from a tetrazine moiety selected from formulae IIIA-F:

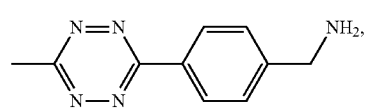
IIIA

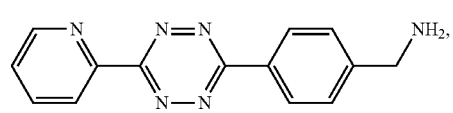
IIIB

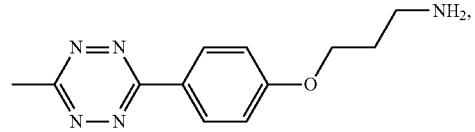
IIIC

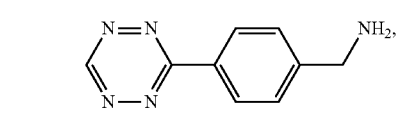
IIID

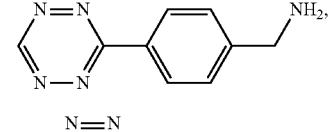
IIIE and

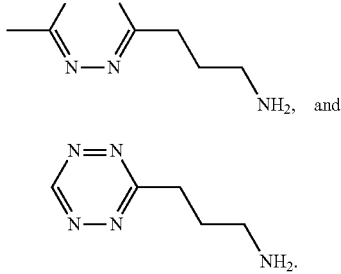
IIIF

In some embodiments, the first compound and the second compound are covalently bound.

In some embodiments, the norbornene moiety and the tetrazine moiety are bound to the first HA chain and to the second HA chain via a covalent bond.

In some embodiments, the covalent bond is selected from the group comprising: amide, amine, ester, ether, carbamide, thiocarbamide, and carbamate.

In some embodiments, the first HA chain and the second HA chain have an average molecular weight Mw of 100,000 to 4,000,000 Daltons (Da).

In some embodiments, the polymer has a phase angle (δ) of 0.1 to 10°.

In some embodiments, the polymer has an elastic modulus (G') of 10 to 1,000 Pa.

In some embodiments, the polymer comprises an HA content of 1 mg/gr to 20 mg/gr.

In some embodiments, the crosslinking degree is determined by $^1$H NMR.

According to another aspect there is provided a composition comprising a polymer of the invention and a pharmaceutically acceptable carrier.

In some embodiments, the composition comprises one or more from:
1) a polymer comprising a linker represented by formula (A);
2) a polymer comprising a linker represented by formula (B);
3) a polymer comprising a linker represented by formula (C);
4) a polymer comprising a linker represented by formula (D).

In some embodiments, the composition further comprises 0.1-30% (w/w) non-cross-linked HA out of the total HA content in the composition.

In some embodiments, the composition further comprises one or more compounds selected from the group consisting of: an amino acid, a mineral, a vitamin, an antioxidant, a nucleic acid, a coenzyme, an enzyme, a growth factor, a protein, an antitumoral drug, a steroid, a non-steroidal anti-inflammatory drug, an antibiotic, an anesthetic agent, an antimicrobial drug, or any combination thereof.

According to another aspect, there is provided a method for filling or volumizing a tissue in a subject in need thereof, comprising administering the composition of the invention, or the polymer of the invention to the tissue, thereby filling or volumizing a tissue in a subject in need thereof.

In some embodiments, the tissue is selected from the group consisting of: skin, gingival, cartilage and ophthalmic tissue, muscles, and subcutaneous tissues.

According to another aspect, there is provided a process for preparing the polymer in an embodiment thereof, the process comprising: mixing a first hyaluronic acid (HA) chain or a derivative thereof and a second HA chain or a derivative thereof, wherein the first HA chain comprises an unsaturated moiety or a derivative thereof and the second HA chain comprises a tetrazine moiety or a derivative thereof wherein the unsaturated moiety or a derivative thereof and the tetrazine moiety or a derivative thereof are present in a molar ratio of 3:1 to 1:3; thereby crosslinking the first HA chain or a derivative thereof and the second HA chain or a derivative thereof.

In some embodiments, the unsaturated moiety comprises a norbornene moiety or a derivative thereof.

In some embodiments, the first HA chain or a derivative thereof and the second HA chain or a derivative thereof have an average molecular weight Mw of 100,000 to 4,000,000 Daltons (Da).

In some embodiments, crosslinking comprises forming a covalent bond between the norbornene moiety or derivative thereof and the tetrazine moiety or derivative thereof.

According to another aspect, there is provided a kit comprising a first HA chain or a derivative thereof coupled to an unsaturated moiety or a derivative thereof, and a second HA chain or a derivative thereof coupled to a tetrazine moiety or a derivative thereof.

In some embodiments, the unsaturated moiety comprises a norbornene moiety or a derivative thereof.

In some embodiments, the kit further comprises a pharmaceutically acceptable carrier.

In some embodiments, the kit further comprises an injecting device.

In some embodiments, the kit further comprises a component selected from the group consisting of: a free HA chain, an amino acid, a mineral, a vitamin, or an anesthetic.

In some embodiments, the kit comprises instructions for:
a. mixing a first HA chain, or a derivative thereof coupled to a norbornene moiety or a derivative thereof and a second HA chain or a derivative thereof coupled to a tetrazine moiety or a derivative thereof in a ratio from 3:1 to 1:3; and
b. applying the composition formed by mixing the first HA chain, or a derivative thereof coupled to the norbornene moiety or a derivative thereof and the second HA chain or a derivative thereof coupled to the tetrazine moiety or a derivative thereof to a filling or volumizing method.

In some embodiments, the kit further comprises instructions for mixing the composition with a free HA chain, an amino acid, a mineral, a vitamin, an anesthetic, or any combination thereof.

In some embodiments, mixing is performed in the injecting device.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
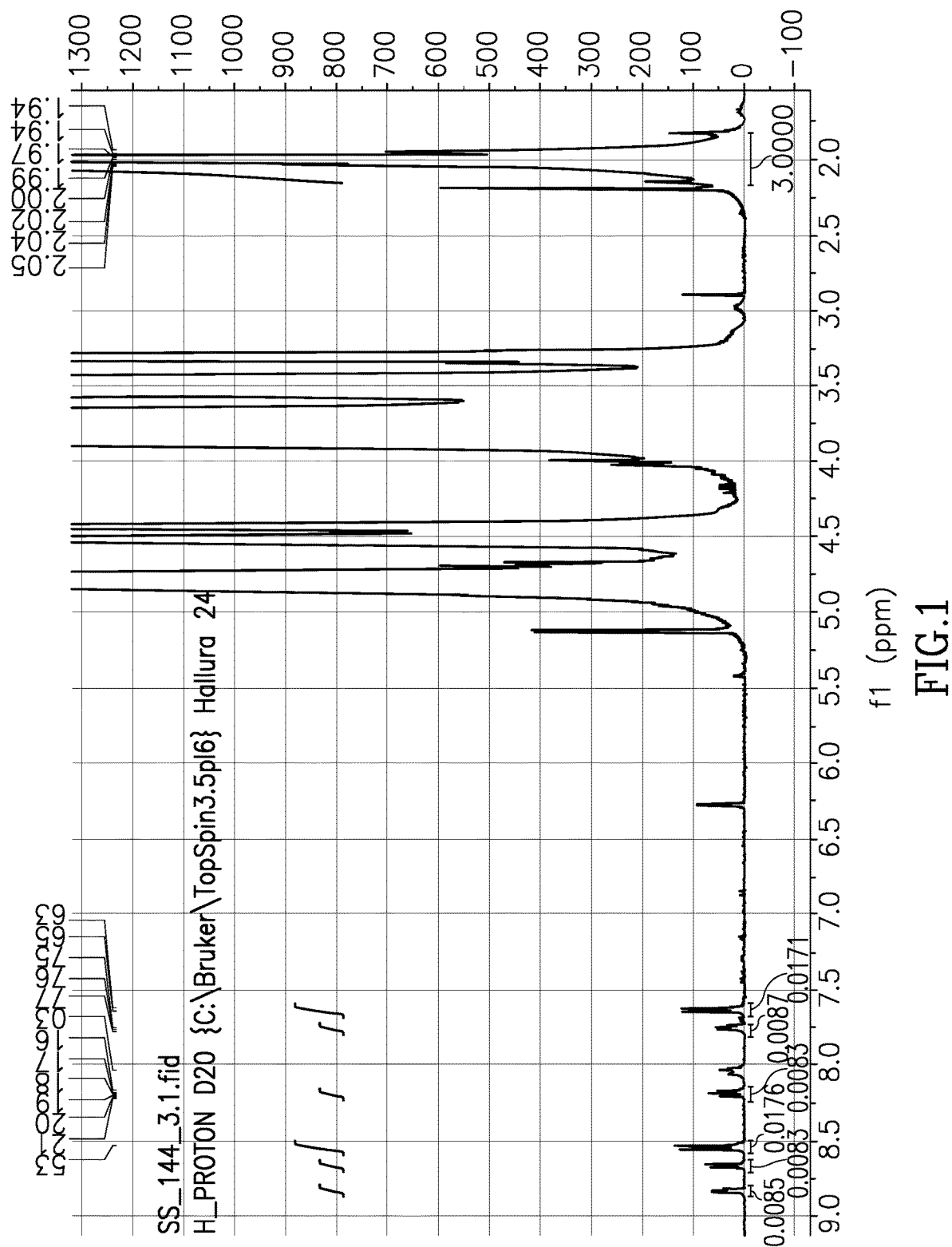
FIG. 1: An $^1$H NMR spectrum of hyaluronic acid modified with tetrazine (HA-tetrazine), showing aromatic peaks of tetrazine, and an aliphatic peak of the N-acetyl glucosamine residue.

In some embodiments, the present invention is directed to a polymer comprising a first hyaluronic acid (HA) chain and a second HA chain crosslinked via a linker comprising an unsaturated moiety or a derivative thereof bound to a tetrazine moiety or a derivative thereof. In some embodiments, the polymer of the invention is characterized by having a crosslinking degree of 0.2 to 4%.

In some embodiments, the unsaturated moiety comprises: an unsaturated cycloalkyl, an unsaturated alkaryl, an unsaturated alkyl or a combination thereof. In some embodiments, the unsaturated moiety comprises a cyclic, or a non-cyclic alkyne. In some embodiments, the unsaturated moiety comprises a cyclic, or a non-cyclic alkene. In some embodiments, the unsaturated moiety comprises an optionally fused cyclic alkene.

In some embodiments, the unsaturated moiety is selected from the group comprising: styrene, cyclohexene, cyclopentene, cyclohexadiene, cyclopentadiene, norbornadiene, fused norbornadiene, norbornene, and fused norbornene, substituted or non-substituted. In exemplary embodiments, the unsaturated moiety is norbornene.

The Polymer

In some embodiments, the invention is directed to a polymer comprising a hyaluronic acid (HA) chain or a derivative thereof. As used herein, HA chain or derivative thereof comprises D-glucuronic acid and N-acetyl-glucosamine.

As used herein, a derivative of HA chain relates to a chemically modified HA. In some embodiments, a chemically modified HA comprises a side chain modification (e.g. acetylation of a hydroxy group, decarboxylation, esterification or amidation of a carboxy group). In some embodiments, a chemically modified HA comprises one or more of the side chain modifications. In some embodiments, the modifications are the same. In some embodiments, the modifications are different. In some embodiments, a chemically modified HA comprises a combination of modified side chains.

In some embodiments, HA chain of the present invention has a molecular weight of 50,000-200,000 Da, 100,000-200,000 Da, 150,000-400,000 Da, 150,000-1,000,000 Da, 250,000-1,500,000 Da, 350,000-5,000,000 Da, 750,000-4,000,000 Da, 50,000-5,000,000 Da, 1,000,000-7,500,000 Da, 2,000,000-10,000,000 Da, 400,000-5,000,000 Da, 650,000-8,000,000 Da, 4,000,000-10,000,000 Da, or 7,500,000-15,000,000 Da. Each possibility represents a separate embodiment of the present invention.

As used herein, the term "molecular weight" encompasses any one of the average weight values selected from: $M_n$ (Number average molar mass), NAMW (Number Average Molecular Weight), $M_w$ (Mass average molar mass), WAMW (Weight Average Molecular Weight), $M_z$ (Z average molar mass), $M_v$ (Viscosity average molar mass), and MWCO (molecular weight cut-off). Unless stated otherwise this term refers to $M_w$.

In one embodiment, the invention is directed to a polymer comprising a polycarboxylated polysaccharide or a derivative thereof having a molecular weight in the ranges specified above.

In some embodiments, the polymer of the present invention comprises one or more HA chains. In some embodiments, "one or more" is two. In some embodiments, two HA chains of the invention are crosslinked. In one embodiment, cross-linking is inter-crosslinking. As defined herein, the term "inter" refers to the formation of a bond between two moieties residing in two different chains, as oppose to the formation of an "intra" bond between two residues residing within the same chain. In some embodiments, crosslinking of two HA chains is via a linker.

A "linker" as defined herein refers to a molecule or macromolecule serving to connect different moieties or functional groups of one or more polycarboxylated polysaccharides. In one embodiment, a linker may also facilitate other functions, including, but not limited to, preserving biological activity, maintaining interactions, and others.

In some embodiments, the polymer of the present invention comprises a first HA chain connected to a second HA chain by one or more linkers, comprising a compound represented by formula (A):

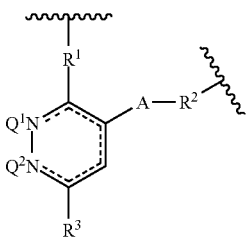

or by formula (B):

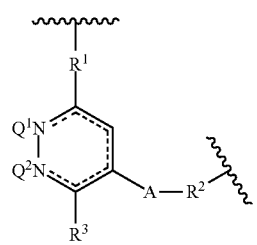

or a combination thereof; wherein:

- - - represents a single or a double bond.

In some embodiments, the polymer of the present invention comprises a first HA chain crosslinked to a second HA chain via one or more linkers, comprising a compound represented by formulae (A) and/or (B).

In some embodiments, $R^1$, $R^2$, or both are selected from the group comprising: a bond, alkyl, alkenyl, cycloalkyl, aryl, heteroaryl, heteroalicyclic, C(O)—NH-alkyl-NH, and alkyl-NZ, wherein Z is a bond, aryl, or heteroaryl.

In some embodiments, A is selected form the group comprising: a bond, alkyl, and aryl.

In some embodiments, $Q^1$, $Q^2$ or both represent hydrogen, or are absent.

In some embodiments, $R^3$ is selected from the group comprising: hydrogen, alkyl, aryl, and heteroaryl substituted or non-substituted.

In some embodiments, the polymer of the present invention comprises a first HA chain connected to a second HA chain by one or more linkers comprising a compound represented by formula (C):

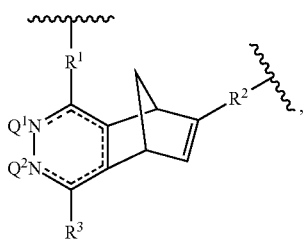

or by formula (D):

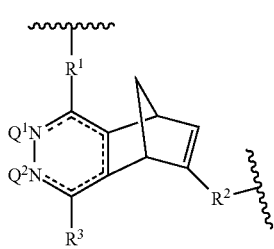

or a combination thereof;
wherein - - - represents a single or a double bond.

In some embodiments, the polymer of the present invention comprises a first HA chain crosslinked to a second HA chain via a linker, comprising a compound represented by formula (C) or (D).

In some embodiments, the linker comprises a first compound derived from an unsaturated moiety and a second compound derived from a tetrazine moiety, as described herein below. In some embodiments, the first compound and the second compound are covalently bound. In some embodiments, the first compound and the second compound are covalently bound, thereby forming a compound represented by any one of formulae (A) to (D).

In some embodiments, $R^1$, $R^2$, and $R^3$, comprise a substituent selected from the group consisting of: alkyl, cycloalkyl, aryl, heteroalicyclic, heteroaryl, alkoxy, hydroxy, phosphonate, thiohydroxy, thioalkoxy, aryloxy, thioaryloxy, amino, nitro, halo, trihalomethyl, cyano, amide, amine, alkanoamine, carboxy, sulfonyl, sulfoxy, sulfinyl, and sulfonamide.

In some embodiments, $Q^1$, $Q^2$ or both represent hydrogen, or are absent.

In some embodiments, the polymer of the present invention comprises a first HA chain connected to a second HA chain by a linker comprising a compound selected from the group consisting of:

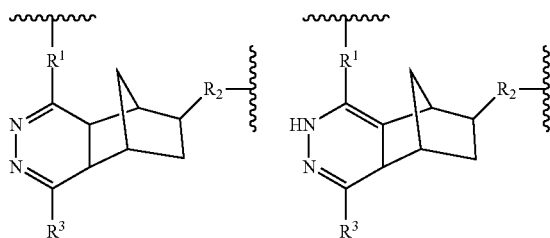

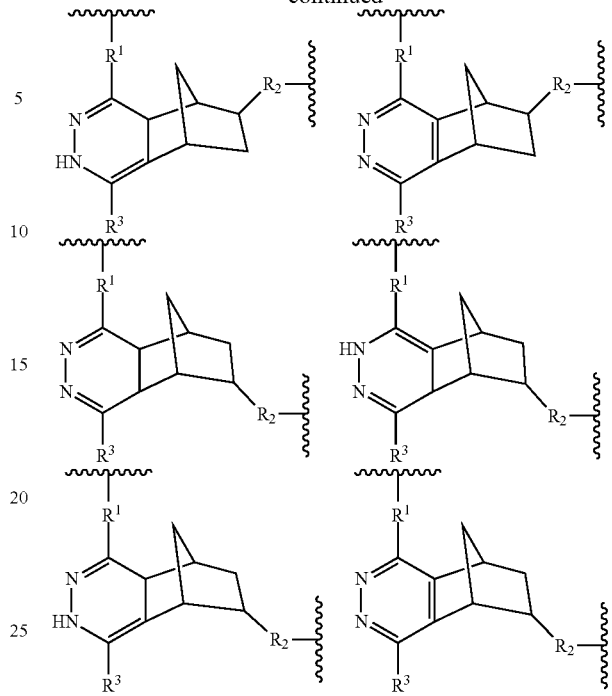

In some embodiments, $R^1$ is selected from the group comprising: —$C_0$-$C_6$alkyl-NZ—, —$C_0$-$C_6$alkyl-O—, and —$C_0$-$C_3$alkyl-C(O)—.

In some embodiments, Z is selected from the group comprising: a bond, aryl, or heteroaryl, wherein the aryl and heteroaryl are optionally substituted with halogen, hydroxy, $C_1$-$C_6$alkyl, $C_1$-$C_6$alkoxy, ($C_1$-$C_6$alkyl)amino, and di($C_1$-$C_6$alkyl)amino;

In some embodiments, $R^2$ is selected from the group comprising: $C_0$-$C_6$alkyl-NZ, —$C_0$-$C_6$alkyl O—, and $C_0$-$C_3$alkyl-C(O)—.

In some embodiments, $R^3$ is selected from the group comprising: hydrogen, $C_1$-$C_6$alkyl, aryl, or heteroaryl, wherein the aryl and heteroaryl are optionally substituted with halogen, hydroxy, $C_1$-$C_6$ alkyl, $C_1$-$C_6$ alkoxy, ($C_1$-$C_6$-alkyl)amino, and di($C_1$-$C_6$alkyl)amino.

In one embodiment, "- - -" refers to a single bond or, in some embodiments to a double bond as feasible.

In some embodiments, $R^1$, $R^2$, or both are selected from the group comprising: —NZ—, —$C_1$-$C_6$ alkyl-NZ—, —O—, —$C_1$-$C_6$ alkyl —O—, —C(O)—, or —$C_1$-$C_3$alkyl-C(O)—; -methyl-O, -pentyl-O—; —C(O)—; and -methyl-C(O)—.

In some embodiments, Z is a bond. In some embodiments, Z is selected from the group comprising: aryl and heteroaryl, phenyl; pyridyl, pyrimidyl, and pyrazinyl; each optionally may be substituted.

Another embodiment provides the linkers comprising the compounds of formulae (C) or (D) according to any preceding embodiment, wherein $R^1$, $R^2$ or both are selected from the group comprising: —NZ—, —$C_1$-$C_6$-alkyl-NZ—, —O—, —$C_1$-$C_6$ alkyl-O—, —C(O)—, or —$C_1$-$C_3$-alkyl-C(O)—; —$C_1$-$C_6$ alkyl-NZ—; $C_1$-$C_3$, alkyl-NZ—; -methyl-NH— or -pentyl-NH—; —$C_1$-$C_6$ alkyl-O—; —$C_1$-$C_3$ alkyl-O—; -methyl-O, or -pentyl-O—; —$C_0$-$C_3$ alkyl-C(O)—; C(O)—; and -methyl-C(O)—.

In some embodiments, $R^3$ is hydrogen.

In some embodiments, $R^3$ is selected from the group comprising: $C_1$-$C_6$ alkyl, aryl, or heteroaryl, wherein the aryl or the heteroaryl may be optionally substituted; aryl or heteroaryl, wherein aryl and heteroaryl are optionally substituted; phenyl; pyridyl, pyrimidyl, or pyrazinyl.

In some embodiments, $R^3$ in the linkers comprising the compounds of formulae (C) or (D) is selected from the group comprising: $C_1$-$C_6$ alkyl, $C_1$-$C_3$ alkyl, and methyl.

In some embodiments, the polymer comprises a plurality of linkers comprising the compounds of formulae (C) or (D).

In some embodiments, the invention is directed to a polymer comprising a first HA chain and a second HA chain, interconnected to one another by a linker resulting in a cyclization such as, and without being bound by any particular mechanism, including an inverse electron-demand Diels-Alder cyclization of an unsaturated moiety (e.g. norbornene moiety) or a derivative thereof, and a tetrazine moiety or a derivative thereof.

In some embodiments, a first HA chain of the invention comprises an unsaturated moiety, as described herein above. In some embodiments, a first HA chain of the invention comprises a styrene moiety or a derivative thereof.

In some embodiments, a styrene moiety is represented by formulae IA-D:

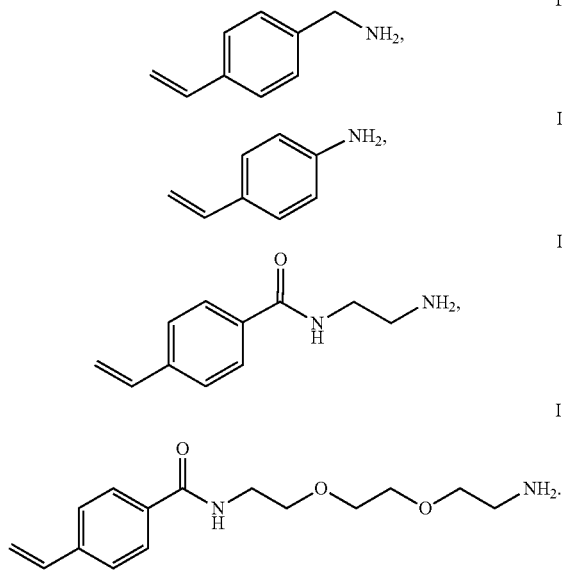

In some embodiments, a derivative of the styrene moiety comprises the styrene moiety of formulae IA-ID bound to the first HA chain via a covalent bond.

Non-limiting examples of covalent bonds include, but are not limited to: amide, amine, ester, ether, carbamide, thiocarbamide, and carbamate.

In some embodiments, the amine of the styrene moiety is covalently bound to the first HA chain. In some embodiments, the styrene moiety is bound to a carboxy group of the first HA chain. In some embodiments, a derivative of the styrene moiety is referred to a styrene moiety (e.g. compound of formula IA) bound to the first HA chain via an amide bond, as represented by formula IE:

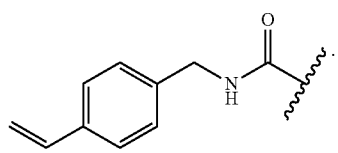

In some embodiments, a first HA chain of the invention comprises a norbornene moiety, or a derivative thereof. In some embodiments, the number of norbornene moieties or derivatives thereof in the first HA chain of the invention may be any integer between 1 and 100,000. In some embodiments, a second HA chain of the invention comprises a tetrazine moiety, or a derivative thereof. In some embodiments, the number of tetrazine moieties or derivatives thereof attached to the second HA chain of the invention can be any integer between 1 and 100,000. In some embodiments, each of the first HA chains comprises, 1-10,000, 1-5,000, 1-1,000, 5,000-50,000, 5,000-10,000, 1,000-10,000, 1,000-5,000, 500-5,000, 500-1000, or 1-500 norbornene moieties or derivatives thereof. In some embodiments, each of the second HA chains comprises 1-100,000, 1-50,000, 1-10,000, 1-5,000, 1-1,000, 5,000-50,000, 5,000-10,000, 1,000-10,000, 1,000-5,000, 500-5,000, 500-1,000, or 1-500 tetrazine moieties or derivatives thereof. Each possibility represents a separate embodiment of the present invention.

In some embodiments, a norbornene moiety is in a conformation of endo, exo or a mixture thereof. Non-limiting examples for a norbornene moiety include, but are not limited to compounds of formulae IIA-IIG:

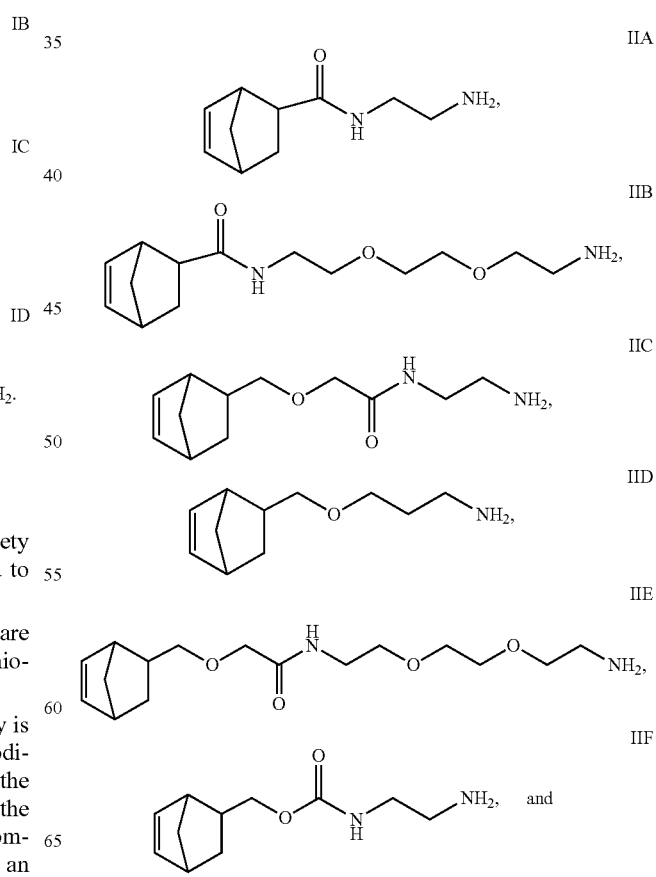

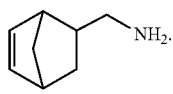

IIG

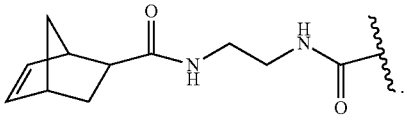

IF

Non-limiting examples for a tetrazine moiety include, but are not limited to compounds of formulae IIIA-IIIF:

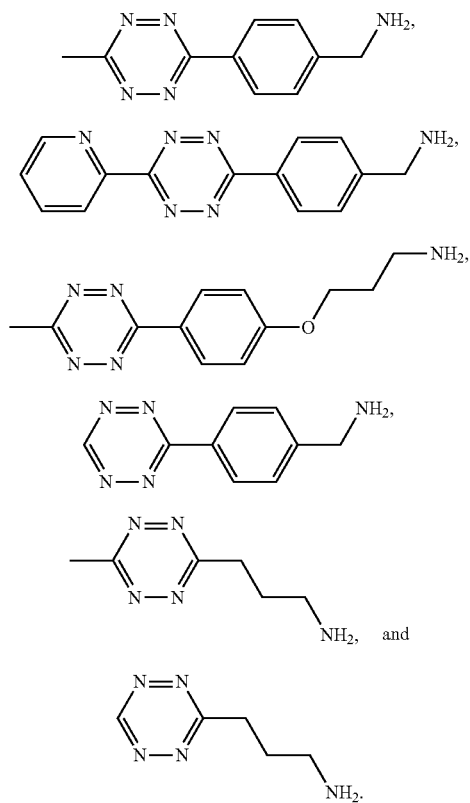

In some embodiments, the norbornene moiety is bound to the first HA chain by reacting the first HA chain and the norbornene moiety (e.g. norbornene methanamine, norbornene methanol) with an appropriate coupling agent.

Non-limiting examples of coupling agents include, but are not limited to, 1-ethyl-3-(3-dimethylamino-propyl)carbodiimide (EDC), carbonyl diimidazole, N,N'-dicyclohexylcarbodiimide (DCC), N,N'-diisopropylcarbodiimide (DIC), 4-(4,6-dimethoxy-1,3,5-triazin-2-yl)-4-methyl-morpholinium chloride (DMTMM) and N,N,N',N'-tetramethyl-O-(1H benzotriazol-1-yl)uronium hexafluorophosphate (HBTU). In one embodiment, a derivative of the tetrazine moiety is related to the tetrazine moiety, as defined herein above, is bound to the second HA chain via a covalent bond. In some embodiments, the covalent bond is as defined herein above.

In some embodiments, a derivative of the tetrazine moiety comprises a tetrazine moiety represented by formulae IIIA-IIIF bound to the second HA chain via a covalent bond. In some embodiments, the amine of the tetrazine moiety is bound to the second HA chain. In some embodiments, the tetrazine moiety is bound to the carboxy group of the second HA chain. In some embodiments, a derivative of the tetrazine moiety is referred to a tetrazine moiety (e.g. a compound of formula IIIB) bound to the second HA chain via an amide bond, as represented by formula IG:

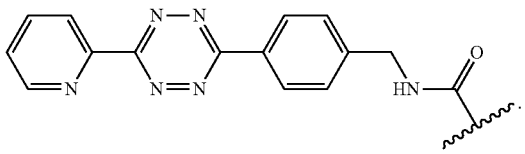

IG

In some embodiments, the norbornene moiety is the compound of formula IIG:

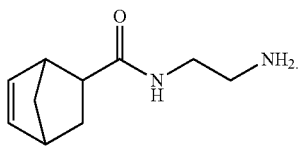 [SMILES: NCCNC(=O)C1CC2C=CC1C2]

In some embodiments, a derivative of the norbornene moiety comprises a norbornene moiety represented by formulae IIA-IIG, bound to the first HA chain via a covalent bond.

In some embodiments, the amine of the norbornene moiety is bound to the first HA chain. In some embodiments, the norbornene moiety is bound to the carboxy group of the first HA chain. In some embodiments, a derivative of the norbornene moiety is referred to a norbornene moiety (e.g. a compound of formula IIG) bound to the first HA chain via an amide bond, as represented by formula IF:

In some embodiments, the tetrazine moiety is bound to the second HA chain by reacting the second HA chain and the tetrazine moiety (e.g. benzyl amine tetrazine), with an appropriate coupling agent.

In some embodiments, the first HA chain coupled to the norbornene moiety or a derivative thereof and the second HA chain coupled to the tetrazine moiety or a derivative thereof, are present in a polymer of the invention at a ratio of 3:1, 3:2, 2:1, 1:1, 1:2, 2:3, or 1:3, including any value and range there between. Each possibility represents a separate embodiment of the present invention. As defined herein, ratio is any ratio selected from: moles, weights, or concentrations.

As defined herein, the term "crosslinking degree" refers to the mole ratio between the linker and the repeating polycarboxylated polysaccharide forming the polymer of the invention. In some embodiments, the crosslinking degree refers to the mole ratio between the linker including the non-reacted norbornene and tetrazine, and the repeating polycarboxylated polysaccharide forming the polymer of the invention. In some embodiments, the crosslinking degree of a polymer of the invention is 0.1% at most, 0.2% at most, 0.5% at most, 0.7% at most, 0.9% at most, 1% at most, 2% at most, 3% at most, 4% at most, 5% at most, 6% at most, 7% at most, 8% at most, 9% at most, 10% at most, or 12% at most. In some embodiments, the crosslinking degree of a polymer of the invention is 0.01-0.1%, 0.01-0.5%, 0.05-0.1%, 0.1-0.3%, 0.1-0.5%, 0.1-0.75%, 0.1-1%, 1-1.75%, 1-2%, 1-2.5%, 2-2.5%, 2.25-3%, 2.5-3.25%, 3-3.75%, 3.6-4.2%, 4-5.25%, 5-6.5%, 6-7.5%, 7-8.5%, 8-9.25%, 9-10.5%, or 10-12.5%. Each possibility represents a separate embodiment of the present invention. In one embodiment, the crosslinking degree of a polymer refers to the calculated mean of crosslinking degree of a plurality of HA chains within a polymer of the invention.

In some embodiments, the polymer of the invention is elastic. As used herein, the elasticity of a polymer is characterized by the elastic modulus (G'). In some embodiments, the term "elastic modulus" means the elastic modulus as determined herein below.

In some embodiments, the polymer of the present invention has an elastic modulus of 10-500 Pa, 20-1,000 Pa, 30-600 Pa, 40-1,000 Pa, 40-5,000 Pa, 50-10,000 Pa, 500-50,000 Pa, 500-10,000 Pa, 500-5,000 Pa, 500-1,000 Pa, 1,000-50,000 Pa, 1,000-10,000 Pa, 1,000-5,000 Pa, 50-20,000 Pa, 500-20,000 Pa, or 1,000-20,000 Pa. In some embodiments, the polymer of the present invention has an elastic modulus up to 10,000 Pa, up to 20,000 Pa, up to 30,000 Pa, up to 40,000 Pa, or up to 50,000 Pa. Each possibility represents a separate embodiment of the present invention.

As defined herein, the term "phase angle" or "δ" refers to degree of viscoelasticity of a material. As would be apparent to one of ordinary skill in the art, δ can be calculated according to the following equation:

$$\delta = \text{Inverse Tangent}\left(\frac{G''}{G'}\right);$$

wherein G" is the viscosity modulus and G' is the elasticity modulus. In some embodiments, G' and G" are obtained by oscillatory rheology and are measured in the viscoelastic domain for low oscillation in stress or amplitude.

In some embodiments, the polymer of the invention has a phase angle (δ) of 0.1-25°, 0.1-0.5°, 0.1-0.9°, 0.5-1°, 0.7-1.5°, 1-2.5°, 2-4.5°, 3-4.75°, 4.7-5.5°, 5-7.5°, 6-8°, 7-8.5°, 8.25-9.5°, 9-10.5°, 9.5-12°. In some embodiments, the polymer of the invention has a phase angel (δ) of 0.1° at most, 0.5° at most, 0.7° at most, 0.9° at most, 1° at most, 1.5° at most, 2° at most, 2.7° at most, 3.2° at most, 4° at most, 4.5° at most, 6° at most, 7.5° at most, 8° at most, 9° at most, 10° at most, 11° at most, or 13° at most. Each possibility represents a separate embodiment of the present invention.

In some embodiments, the present invention is directed to a process of preparing the polymer of the invention, the process comprising the steps of: (i) linking an unsatured moiety (e.g. norbornene moiety) (or a derivative thereof) to a first hyaluronic acid (HA) chain (or a derivative thereof) and linking a tetrazine moiety (or a derivative thereof) to a second HA chain (or a derivative thereof); (ii) mixing the first (HA) chain (or a derivative thereof) comprising the norbornene moiety (or a derivative thereof) and the second HA chain (or a derivative thereof) comprising the tetrazine moiety (or a derivative thereof); and (iii) crosslinking the first HA chain to the second HA chain.

In some embodiments, the step (i) further comprises purifying the HA chain linked to the unsaturated moiety or to the tetrazine moiety.

Following the attachment of the unsaturated moiety or the tetrazine moiety to the HA chain, the resulting product is purified from unreacted starting materials, as well as from inorganic salts. Purification can be performed by any one of the methods known in the art, such as dialysis, precipitation, ultrafiltration or tangential flow filtration.

In some examples, the crosslinking reaction occurs at a usable range of temperature and conditions for forming polymers and occurs without the input of external energy. In one embodiment, the crosslinking reaction is heated to increase reaction efficacy.

In some embodiments, the process for preparing the polymer of the invention comprises a spontaneous crosslinking reaction. In some embodiments, by "spontaneous chemical reaction" it is meant to refer to a process that is not assisted by e.g., light, heat, or radicals. In some embodiments, the crosslinking reaction may occur in water, in aqueous buffers or in cell culture media. Non-limiting examples for culture media include, but are not limited to, phosphate buffered saline, Hank's balanced salt solution, Dulbecco's Modified Eagle Medium, and the like. In some embodiments, the cross-linking can occur in organic solvents. Non-limiting examples for organic solvents include, but are not limited to methanol, ethanol, dichloromethane, dimethylformamide, and the like.

In some embodiments, the cross-linking reaction can occur at a wide range of temperatures of at least −80° C., at least −50° C., at least −20° C., at least 0° C., at least 4° C., at least 22° C., at least 37° C., or at least 45° C., and not more than 60° C. In some embodiments, the cross-linking reaction can occur at a wide range of temperatures of (−80)–(−50) ° C., (−60)–(−15) ° C., (−20)–(−4) ° C., (−5)–0° C., (−2)–4° C., 2-8° C., 5-20° C., 15-30° C., 25-40° C., or 35-55° C.

In some embodiments, the steps (ii) and (iii) are performed in-situ, so as to form the cross-linked polymer by mixing the first (HA) chain and the second (HA) chain. In some embodiments, the preparation process is devoid of a post-processing step such as sieving or homogenization.

In some embodiments of the preparation process, after the cross-linking step, unreacted norbornene or a derivative thereof and/or tetrazine or a derivative thereof may remain attached to the HA chains. As defined herein, the term "unreacted" refers to a norbornene moiety or a derivative thereof and/or tetrazine moiety or derivative thereof which are not bound to another HA chain or moiety.

In some embodiments, the norbornene or the derivative thereof and/or the tetrazine or the derivative thereof may be modified. In some embodiments, post-crosslinking reaction modification comprises binding of one or more molecules to the unbound norbornene or the derivative thereof and/or the unbound tetrazine or the derivative thereof on the cross-linked polymer.

Non-limiting examples for the one or more molecules include, but are not limited to: amino acids, anesthetic agents, minerals, vitamins, and others. The amount of unreacted norbornene or a derivative thereof and/or tetrazine or a derivative thereof on the HA chains can be modulated by varying the ratios of the first HA chain to the second HA chain or vice versa during the cross-linking reaction.

Compositions

In some embodiments, the present invention is directed to a composition comprising the polymer of the invention.

In some embodiments, the composition of the present invention comprises cross-linked and non-cross-linked HA. In some embodiments, the total HA polymer content (the cross-linked HA and the non-crossed linked HA) of the composition is present at a concentration of: 1 mg/gr at most, 5 mg/gr at most, 7 mg/gr at most, 8.5 mg/gr at most, 10 mg/gr at most, 12 mg/gr at most, 15 mg/gr at most, 17 mg/gr at most, 18.5 mg/gr at most, 20 mg/gr at most, 22 mg/gr at most, or 25 mg/gr at most. In some embodiments, the total HA polymer content of the composition is 1-2.5 mg/gr, 3-5 mg/gr, 4-7 mg/gr, 6-9 mg/gr, 8-12 mg/gr, 10-13 mg/gr, 12-15 mg/gr, 14-17 mg/gr, 16-19 mg/gr, 18-22 mg/gr, or 20-25 mg/gr. Each possibility represents a separate embodiment of the present invention.

According to another embodiment, the invention provides a pharmaceutical composition comprising a therapeutically effective amount of the polymer of the present invention, and a pharmaceutically acceptable carrier and/or diluent. In some embodiments, the pharmaceutical composition may facilitate administration of a polymer to an organism.

In some embodiments, the composition of the present invention further comprises an amino acid. In some embodiments, the amino acid comprises any amino acid, naturally occurring or non-naturally occurring. Non-limiting examples for non-naturally occurring amino acids, include, but are not limited to, D-amino acids, hydroxylysine, 4-hydroxyproline, N-Cbz-protected aminovaleric acid (Nva), ornithine (O), aminooctanoic acid (Aoc), 2,4-diaminobutyric acid (Abu), homoarginine, norleucine (Nle), N-methylaminobutyric acid (MeB), 2-naphthylalanine (2Np), aminoheptanoic acid (Ahp), phenylglycine, β-phenylproline, tert-leucine, 4-aminocyclohexylalanine (Cha), N-methyl-norleucine, 3,4-dehydroproline, N,N-dimethylaminoglycine, N-methylaminoglycine, 4-aminopipedine-4-carboxylic acid, 6-aminocaproic acid, trans-4-(aminomethyl)-cyclohexanecarboxylic acid, 2-,3-, and 4-(aminomethyl)-benzoic acid, 1-aminocyclopentanecarboxylic acid, 1-aminocyclopropanecarboxylic acid, cyano-propionic acid, 2-benzyl-5-aminopentanoic acid, Norvaline (Nva), 4-O-methyl-threonine (TMe), 5-O-methyl-homoserine (hSM), tert-butyl-alanine (tBu), cyclopentyl-alanine (Cpa), 2-amino-isobutyric acid (Aib), N-methyl-glycine (MeG), N-methyl-alanine (MeA), N-methyl-phenylalanine (MeF), 2-thienyl-alanine (2Th), 3-thienyl-alanine (3Th), O-methyl-tyrosine (YMe), 3-Benzothienyl-alanine (Bzt) and D-alanine (DAl). In some embodiments, the amino acid is an oligomer, or a dimer of amino acids linked by a peptide bond. In some embodiments, the oligomer is a trimer, a tetramer, a pentamer, a hexamer, a heptamer, an octamer, a nonamer, a decamer, or, in some embodiments, is a polymer having more than 11 amino acids bound to one another by peptide bonds. In some embodiments, amino acids are included in the composition form a peptide, a polypeptide or a protein. In some embodiments, the peptide, polypeptide or the protein included in a composition of the present invention, is in the form selected from, without being limited thereto, native, denatured, neutralized, digested, cross-linked, un-folded, reduced, oxidized, or inactivated form.

In some embodiments, the composition of the present invention further comprises a mineral or a plurality of minerals. Non-limiting examples for a mineral include, but are not limited to: Potassium, Chloride, Sodium, Calcium, Phosphorus, Magnesium, Iron, Zinc, Manganese, Copper, Iodine, Chromium, Molybdenum, Selenium or Cobalt.

In some embodiments, the composition of the present invention further comprises a vitamin. Non-limiting examples of vitamins include, but are not limited to: Vitamin A (Retinol, retinal and four carotenoids including beta carotene), Vitamin $B_1$ (Thiamine), Vitamin $B_2$ (Riboflavin), Vitamin $B_3$ (Niacin, niacinamide, Nicotinamide riboside), Vitamin $B_5$ (Pantothenic acid), Vitamin $B_6$ (Pyridoxin, pyridoxamine, pyridoxal), Vitamin $B_7$ (Biotin), Vitamin $B_9$ (Folates), Vitamin $B_{12}$ (Cyanocobalamin, hydroxocobalamin, methylcobalamin, adenosylcobalamin), Vitamin C (Ascorbic acid), Vitamin D (Cholecalciferol ($D_3$), Ergocalciferol ($D_2$)), Vitamin E (Tocopherols, tocotrienols), or Vitamin K (Phylloquinone, menaquinones).

In some embodiments, the composition of the present invention further comprises an anesthetic agent. As used herein, the term "anesthetic" refers to any molecule or substance which prevents pain such as during surgery, or completely blocks any feeling. In one embodiment, the anesthetic agent is general anesthetic agent. In one embodiment, the anesthetic agent is a local anesthetic agent. In some embodiment, a local anesthetic agent induces a reversible loss of sensation limited to a certain region of the body while maintaining consciousness.

Non-limiting examples for anesthetic agents include, but are not limited to articaine, procaine, amethocaine, lidocaine, bupivacaine, levobupivacaine, ropivacaine, mepivacaine, dibucaine and cocaine. In some embodiments, the composition of the present invention comprises 0.01-0.1% (w/w), 0.05-0.15% (w/w), 0.1-0.3% (w/w), 0.2-0.5% (w/w), 0.4-0.7% (w/w), 0.6-0.85% (w/w), 0.8-1.25% (w/w), 1-1.5% (w/w), 1.4-2% (w/w), 1.75-3% (w/w), 2.5-3.75% (w/w), 3.5-4.5% (w/w), or 4.25-5.25% (w/w) of an anesthetic agent. In some embodiments, the composition of the present comprises at most 0.01% (w/w), at most 0.05% (w/w), at most 0.75% (w/w), at most 1% (w/w), at most 1.5% (w/w), at most 2% (w/w), at most 3% (w/w), at most 4% (w/w), or at most 5.5% (w/w) of an anesthetic agent. Each possibility represents a separate embodiment of the present invention.

In some embodiments, the composition of the present invention further comprises non-cross-linked HA. In some embodiments, non-cross-linked HA refers to any HA polymer which is not interconnected to another polymer e.g., another HA polymer. In some embodiments, the term "interconnected" refers to a covalent bond formed by an unsaturated moiety (e.g. norbornene moiety) or a derivative thereof and a tetrazine moiety or a derivative thereof. In some embodiments, as defined herein, the % of non-cross-linked HA is the calculated proportion of the non-cross-linked HA out of the total HA content in the final product (i.e., the composition). In some embodiments, the composition comprises a total HA content of 1 to 6 mg/gr, 2 to 7 mg/gr, 3 to 8 mg/gr, 4 to 9 mg/gr, 5 to 10 mg/gr, 6 to 11 mg/gr, 7 to 12 mg/gr, 8 to 13 mg/gr, 9 to 14 mg/gr, 10 to 15 mg/gr, 11 to 16 mg/gr, 12 to 17 mg/gr, 13 to 18 mg/gr, 14 to 19 mg/gr, 15 to 20 mg/gr, 16 to 21 mg/gr, 17 to 22 mg/gr, 18 to 25 mg/gr, or any range therebetween. In some embodiments, the non-cross-linked HA content in the composition of the present invention is: 5% at most, 7% at most, 10% at most, 15% at most, 20% at most, 25% at most, 27% at most, 30% at most, or 35%. In some embodiments, the non-cross-linked HA is present in the composition at a concentration of: 1-5%, 2.5-7%, 4-9%, 8-12%, 10-16%, 15-20%, 18-25%, 22-28%, or 27-35%. Each possibility represents a separate embodiment of the present invention.

In another embodiment, the pharmaceutical composition of the invention may be formulated in the form of a pharmaceutically acceptable salt of the polymer of the present invention. In another embodiment, pharmaceutically acceptable salts include salts derived from non-toxic inorganic or organic acids such as hydrochloric, phosphoric, acetic, oxalic, tartaric acids, and the like. In some embodiments, the salts are formed with free carboxyl groups such as salts derived from non-toxic inorganic or organic bases such as sodium, potassium, ammonium, calcium, ferric hydroxides, isopropylamine, triethylamine, 2-ethylamino ethanol, histidine, procaine, and the like.

As used herein, the term "carrier" refers to a diluent, adjuvant, excipient, or vehicle administered with the disclosed compound. Such pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerin, propylene glycol or other synthetic solvents. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; and agents for the adjustment of tonicity such as sodium chloride or dextrose are also envisioned. The carrier may comprise, in total, from about 0.1% to about 99.9% by weight of the pharmaceutical compositions presented herein.

As used herein, the term "pharmaceutically acceptable" means suitable for administration to a subject, e.g., a human. For example, the term "pharmaceutically acceptable" can mean approved by a regulatory agency of the Federal or a state government or listed in the U.S. Pharmacopeia or other generally recognized pharmacopeia for use in animals, and more particularly in humans.

In another embodiment, the composition of the invention takes the form of solutions, suspensions, emulsions, tablets, powders, gels, foams, pastes, sustained-release formulations and the like. Examples of suitable pharmaceutical carriers are described in: Remington's Pharmaceutical Sciences" by E. W. Martin, the contents of which are hereby incorporated by reference herein. Such compositions will contain a therapeutically effective amount of the polymer of the invention, preferably in a substantially purified form, together with a suitable amount of carrier so as to provide the form for proper administration to the subject.

According to an embodiment of the invention, a pharmaceutical composition contains 0.1-95% of the polymer(s) of the present invention. According to another embodiment of the invention, a pharmaceutical composition contains 1-70% of the polymer. According to another embodiment of the invention, the composition or formulation to be administered may contain a quantity of polymers, according to embodiments of the invention in an amount effective to treat the condition or disease of the subject being treated.

An embodiment of the invention relates to polymer of the present invention, presented in unit dosage form and prepared by any of the methods well known in the art of pharmacy. In an embodiment of the invention, the unit dosage form is in the form of a tablet, capsule, lozenge, ampoule, vial or pre-filled syringe. In addition, in vitro assays may optionally be employed to help identify optimal dosage ranges. The precise dose to be employed in the formulation will also depend on the route of administration, and the nature of the disease or disorder, and should be decided according to the judgment of the practitioner and each patient's circumstances. Effective doses can be extrapolated from dose-response curves derived from in-vitro or in-vivo animal model test bioassays or systems.

According to one embodiment, the composition of the present invention is administered in the form of a pharmaceutical composition comprising at least one of the active components of this invention (the polymer) together with a pharmaceutically acceptable carrier or diluent. In another embodiment, the composition of this invention can be administered either individually or together in any conventional transdermal dosage form.

As used herein, the terms "administering", "administration", and like terms refer to any method which, in sound medical practice, delivers a composition containing an active agent to a subject in such a manner as to provide a therapeutic effect.

Depending on the location of the tissue of interest, the polymer of the present invention can be administered in any manner suitable for the provision of the polymer to the tissue of interest. Thus, for example, a composition containing the polymer of the present invention can be introduced, for example, injected into the tissue of interest which will distribute the polymer in the tissue.

In some embodiments, the pharmaceutical composition comprising the polymer is administered via ophthalmic, transdermal, intradermal, subcutaneous, intramuscular, or intraperitoneal routes of administration. The route of administration of the pharmaceutical composition will depend on the disease or condition to be treated. Suitable routes of administration include, but are not limited to, parenteral injections, e.g., intradermal, intravenous, intramuscular, intralesional, subcutaneous, intrathecal, and any other mode of injection as known in the art. Although the bioavailability of polymers administered by other routes can be lower than when administered via parenteral injection, by using appropriate formulations it is envisaged that it will be possible to administer the composition of the invention via transdermal, oral, rectal, vaginal, topical, nasal, inhalation and ocular modes of treatment.

For topical application, a polymer of the present invention can be combined with a pharmaceutically acceptable carrier so that an effective dosage is delivered, based on the desired activity. The carrier can be in the form of, for example, and not by way of limitation, an ointment, cream, gel, paste, foam, aerosol, suppository, pad or gelled stick.

According to some embodiments, the polymer of the present invention, can be delivered in a controlled release system. In yet another embodiment, a controlled release system can be placed in proximity to a therapeutic target, thus requiring only a fraction of the systemic dose.

In one embodiment, it will be appreciated that the polymer of the present invention can be provided to the individual with additional active agents to achieve an improved therapeutic effect as compared to treatment with each agent by itself. In another embodiment, measures (e.g., dosing and selection of the complementary agent) are taken to adverse side effects which are associated with combination therapies.

In one embodiment, depending on the severity and responsiveness of the condition to be treated, dosing can be of a single or a plurality of administrations, with course of treatment lasting from several days to several weeks or until cure is affected or diminution of the disease state is achieved.

In some embodiments, the polymer is administered in a therapeutically safe and effective amount. As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the presently described manner. In another embodiment, a therapeutically effective amount of the polymer is the amount of the polymer necessary for the in vivo measurable expected biological or therapeutic effect. The actual amount administered, and the rate and time-course of administration, will depend on the nature and severity of the condition being treated. Prescription of treatment, e.g. decisions on dosage, timing, etc., is within the responsibility of general practitioners or specialists, and typically takes account of the disorder to be treated or the defect to be corrected, the condition of the individual patient, the site of delivery, the method of administration and other factors known to practitioners. Examples of techniques and protocols can be found in Remington: The Science and Practice of Pharmacy, $21^{st}$ Ed., Lippincott Williams & Wilkins, Philadelphia, Pa., (2005). In some embodiments, preparation of effective amount or dose can be estimated initially from in vitro assays. In one embodiment, a dose can be formulated in animal models and such information can be used to more accurately determine useful doses in humans.

In one embodiment, toxicity and therapeutic efficacy of the active ingredients described herein can be determined by standard pharmaceutical procedures in vitro, in cell cultures or experimental animals. In one embodiment, the data obtained from these in vitro and cell culture assays and animal studies can be used in formulating a range of dosage for use in human. In one embodiment, the dosages vary depending upon the dosage form employed and the route of administration utilized. In one embodiment, the exact formulation, route of administration and dosage can be chosen by the individual physician in view of the patient's condition. [See e.g., Fingl, et al., (1975) "The Pharmacological Basis of Therapeutics", Ch. 1 p. 1].

Pharmaceutical compositions containing the presently described polymer as the active ingredient can be prepared according to conventional pharmaceutical compounding techniques. See, for example, Remington's Pharmaceutical Sciences, 18th Ed., Mack Publishing Co., Easton, Pa. (1990). See also, Remington: The Science and Practice of Pharmacy, 21st Ed., Lippincott Williams & Wilkins, Philadelphia, Pa. (2005).

In one embodiment, composition including the preparation of the present invention formulated in a compatible pharmaceutical carrier is prepared, placed in an appropriate container, and labeled for treatment of an indicated condition.

In one embodiment, composition of the present invention is presented in a pack or dispenser device, such as an FDA approved kit, which contains, one or more unit dosages forms containing the active ingredient. In one embodiment, the pack, for example, comprises metal or plastic foil, such as a blister pack. In one embodiment, the pack or dispenser device is accompanied by instructions for administration. In one embodiment, the pack or dispenser is accommodated by a notice associated with the container in a form prescribed by a governmental agency regulating the manufacture, use or sale of pharmaceuticals, which notice is reflective of approval by the agency of the form of the compositions or human or veterinary administration. Such notice, in one embodiment, is labeling approved by the U.S. Food and Drug Administration for prescription drugs or of an approved product insert.

Methods of Use

In some embodiments, there present invention is directed to a method for filling or volumizing a tissue in a subject in need thereof, the method comprising administering to the subject a pharmaceutical composition comprising a therapeutically effective amount of a polymer of the invention.

In some embodiments, a filling or a volumizing method, as defined herein, refers to the injection of a soft filling material into a skin tissue. In some embodiments, the filling is filling wrinkles, such as facial wrinkles. In some embodiments, filling is restoring a smooth appearance or texture of the skin.

In some embodiments, the method is directed to injection of a polymer or a composition of the present invention into a skin tissue. In some embodiments, the method is directed to injection of a polymer or a composition of the present invention into a gingival tissue. In some embodiments, the method is directed to injection of a polymer or a composition of the present invention into a cartilage tissue. In some embodiments, the method is directed to injection of a polymer or a composition of the present invention into an ophthalmic tissue.

According to some embodiments, injection can be performed according to any method and using any injecting device known in the art. Non-limiting examples of injecting devices include, but are not limited to the use of syringes, microsyringes, needleless devices, microneedling, needles, cannula and catheters. Non-limiting examples of needle gauges include but are not limited to, 18 G, 19 G, 20 G, 21 G, 22 G, 23 G, 24 G, 25 G, 26 G, 27 G, 28 G, 29 G, 30 G, 31 G, 32 G, 33 G, or 34 G.

In some embodiments, the method of the present invention is directed to treating arthritis in a subject in need thereof. Non-limiting examples for arthritis include, but are not limited to, acute infectious arthritis, calcium pyrophosphate arthritis, arthritis of the temporomandibular joint (TMJ), reactive arthritis, psoriatic arthritis, chronic infectious arthritis, juvenile idiopathic arthritis (JIA), rheumatoid arthritis (RA), or prosthetic joint infectious arthritis.

In one embodiment, the method of the present invention is directed to treating a subject afflicted with osteoarthritis.

In some embodiments, the method of the present invention is directed to preventing or treating an ophthalmic tissue damage in a subject prior to or after a surgical procedure.

In some embodiments, the method is directed to topical application of a polymer or a composition of the present invention. In some embodiments, the polymer of the present invention is applied on a skin tissue. In some embodiments, the method is directed to promoting/enhancing wound healing, in a subject in need thereof. In some embodiments, the method is directed to promoting/enhancing wound closure, in a subject in need thereof.

In one embodiment, the polymer of the present invention is provided to the subject per se. In one embodiment, one or more of the polymers of the present invention are provided to the subject per se. In one embodiment, the polymer of the present invention is provided to the subject as part of a pharmaceutical composition where it is mixed with a pharmaceutically acceptable carrier. In one embodiment, one or more of the polymers of the present invention are provided to the subject as part of a pharmaceutical composition where they are mixed with a pharmaceutically acceptable carrier.

The term "subject" as used herein refers to an animal, more particularly to non-human mammals and human organism. Non-human animal subjects may also include prenatal forms of animals, such as, e.g., embryos or fetuses. Non-limiting examples of non-human animals include but are not limited to: horse, cow, camel, goat, sheep, dog, cat, non-human primate, mouse, rat, rabbit, hamster, guinea pig, or pig. In one embodiment, the subject is a human. Human subjects may also include fetuses. In one embodiment, a subject in need thereof is a subject afflicted with and/or at risk of being afflicted with a condition associated with arthritis. In some embodiments, a subject in need thereof is a subject afflicted by reduction of tissue volume. In some embodiments, reduction of tissue volume is referred to as "devolumization". In some embodiments, tissue devolumization comprises fat loss, water loss, moisture loss, extracellular matrix degradation, collagen loss, or others. In some embodiments, devolumization induces skin sagging and descent. In some embodiments, a subject suffers from burns. In some embodiments, a subject in need of a method for wound closure suffers from leakage of body fluids, such as bleeding. As used herein, the terms "treatment" or "treating" of a disease, disorder, or condition encompasses alleviation of at least one symptom thereof, a reduction in the severity thereof, or inhibition of the progression thereof. Treatment does not mean that the disease, disorder, or condition is totally cured. To be an effective treatment, a useful composition herein needs only to reduce the severity of a disease, disorder, or condition, reduce the severity of symptoms associated therewith, or provide improvement to a patient or subject's quality of life.

As used herein, the term "prevention" of a disease, disorder, or condition encompasses the delay, prevention, suppression, or inhibition of the onset of a disease, disorder, or condition. As used in accordance with the presently described subject matter, the term "prevention" relates to a process of prophylaxis in which a subject is exposed to the presently described polymer or composition comprising the polymer prior to the induction or onset of the disease/disorder process. In any case, the term prophylaxis can be applied to encompass prevention. Conversely, the term "treatment" refers to the clinical application of active agents to combat an already existing condition whose clinical presentation has already been realized in a patient.

As used herein, the term "condition" includes anatomic and physiological deviations from the normal that constitute an impairment of the normal state of the living animal or one of its parts, that interrupts or modifies the performance of the bodily functions.

The Kit

According to some embodiments, the present invention provides a kit comprising a first HA chain or a derivative thereof coupled to an unsaturated moiety or a derivative thereof and a second HA chain or a derivative thereof coupled to a tetrazine moiety or a derivative thereof. The terms "HA chain or a derivative thereof", "unsaturated moiety or a derivative thereof" and "tetrazine moiety or a derivative thereof" are as defined herein above In some embodiments, the present invention provides a kit comprising a first HA chain or a derivative thereof coupled to a norbornene moiety or a derivative thereof and a second HA chain or a derivative thereof coupled to a tetrazine moiety or a derivative thereof, and a device for injecting in or through the skin or a device for microperforation of the skin, designated to the administration of the dose.

According to some embodiments, the present invention provides a kit comprising polymer comprising a first hyaluronic acid (HA) chain or a derivative thereof and a second HA chain or a derivative thereof, wherein said first HA chain and said second HA chain are crosslinked via one or more linkers, wherein said one or more linkers comprise norbornene moiety or a derivative thereof coupled to a tetrazine moiety or a derivative thereof, and wherein said polymer is characterized by a crosslinking degree of 0.2 to 4%, as determined by $^1$H NMR In some embodiments, an injecting device is as disclosed above. In one embodiment, an injecting device is disposable. In some embodiments, the injecting device is suitable for an intraepidermal and/or intradermal and/or subcutaneous injection. In some embodiments, the injecting device is suitable for mesotherapy technique. As used herein, the term "mesotherapy" refers to a non-surgical cosmetic medicine treatment.

In some embodiments, the kit further comprises an amino acid as disclosed above.

In some embodiments, the kit further comprises a mineral as disclosed above.

In some embodiments, the kit further comprises a vitamin as disclosed above.

In some embodiments, the kit further comprises an anesthetic as disclosed above.

In some embodiments, the kit further comprises a pharmaceutically acceptable carrier as disclosed above.

In some embodiments, the packaging is scored so as to allow the first HA chain or a derivative thereof coupled to a norbornene moiety or a derivative thereof, the second HA chain or a derivative thereof coupled to a tetrazine moiety or a derivative thereof, the free HA chain, the amino acid, the vitamin, the mineral, the anesthetic, or any combination thereof to be sampled.

In one embodiment, a packaging is in the form of an ampoule, a bottle or a capsule. In one embodiment, a capsule is a soft capsule.

In some embodiments, the components of the kit disclosed above are sterile. As used herein, the term "sterile" refers to a state of being free from biological contaminants. Any method of sterilization is applicable and would be apparent to one of ordinary skill in the art.

In some embodiments, the kit further comprises a free HA chain or a derivative thereof. As defined herein, a free HA chain or a derivative thereof is an HA chain not coupled to a tetrazine moiety, a norbornene moiety, or derivatives thereof.

According to some embodiments, the kit is utilized by mixing a first HA chain or a derivative thereof coupled to a norbornene moiety or a derivative thereof and a second HA chain or a derivative thereof coupled to a tetrazine moiety or a derivative thereof, and applying the composition formed by mixing a first HA chain or a derivative thereof coupled to a norbornene moiety or a derivative thereof and a second HA chain or a derivative thereof coupled to a tetrazine moiety or a derivative thereof to a filling or volumizing method.

In some embodiments, the kit is utilized by further mixing the composition formed by mixing a first HA chain or a derivative thereof coupled to a norbornene moiety or a derivative thereof and a second HA chain or a derivative thereof coupled to a tetrazine moiety or a derivative thereof, and a free HA chain, an amino acid, a vitamin, a mineral, an anesthetic, or any combination thereof and applying the composition formed by mixing the first HA chain or a derivative thereof coupled to a norbornene moiety or a derivative thereof and the second HA chain or a derivative thereof coupled to a tetrazine moiety or a derivative thereof, and the free HA chain, the amino acid, the vitamin, the mineral, the anesthetic, or any combination thereof to a filling or volumizing method.

In some embodiments, the kit comprises instructions for mixing a first HA chain or a derivative thereof coupled to a norbornene moiety or a derivative thereof and a second HA chain or a derivative thereof coupled to a tetrazine moiety or a derivative thereof in a ratio of about 3:1. In some embodiments, the kit comprises instructions for mixing a first HA chain or a derivative thereof coupled to a norbornene moiety or a derivative thereof and a second HA chain or a derivative thereof coupled to a tetrazine moiety or a derivative thereof in a ratio of about 3:2. In some embodiments, the kit comprises instructions for mixing a first HA chain or a derivative thereof coupled to a norbornene moiety or a derivative thereof and a second HA chain or a derivative thereof coupled to a tetrazine moiety or a derivative thereof in a ratio of about 2:1. In some embodiments, the kit comprises instructions for mixing a first HA chain or a derivative thereof coupled to a norbornene moiety or a derivative thereof and a second HA chain or a derivative thereof coupled to a tetrazine moiety or a derivative thereof in a ratio of about 1:1. In some embodiments, the kit comprises instructions for mixing a first HA chain or a derivative thereof coupled to a norbornene moiety or a derivative thereof and a second HA chain or a derivative thereof coupled to a tetrazine moiety or a derivative thereof in a ratio of about 1:2. In some embodiments, the kit comprises instructions for mixing a first HA chain or a derivative thereof coupled to a norbornene moiety or a derivative thereof and a second HA chain or a derivative thereof coupled to a tetrazine moiety or a derivative thereof in a ratio of about 2:3. In some embodiments, the kit comprises instructions for mixing a first HA chain or a derivative thereof coupled to a norbornene moiety or a derivative thereof and a second HA chain or a derivative thereof coupled to a tetrazine moiety or a derivative thereof in a ratio of about 1:3. In some embodiments, the kit comprises instructions for mixing a first HA chain or a derivative thereof coupled to a norbornene moiety or a derivative thereof and a second HA chain or a derivative thereof coupled to a tetrazine moiety or a derivative thereof in any of the ratios mentioned above or any ratio therebetween.

In some embodiments, the kit comprises instructions for mixing a first HA chain or a derivative thereof coupled to a norbornene moiety or a derivative thereof and a second HA chain or a derivative thereof coupled to a tetrazine moiety or a derivative thereof and a free HA chain, an amino acid, a vitamin, a mineral, an anesthetic, or any combination thereof.

In some embodiments, the kit is utilized by mixing a first HA chain or a derivative thereof coupled to a norbornene moiety or a derivative thereof and a second HA chain or a derivative thereof coupled to a tetrazine moiety or a derivative thereof and a free HA chain, an amino acid, a vitamin, a mineral, an anesthetic, or any combination thereof, wherein mixing comprises introducing the components in the injecting device.

In some embodiments, the kit comprises instructions for mixing a first HA chain or a derivative thereof coupled to a norbornene moiety or a derivative thereof and a second HA chain or a derivative thereof coupled to a tetrazine moiety or a derivative thereof and a free HA chain, an amino acid, a vitamin, a mineral, an anesthetic, or any combination thereof, wherein mixing is performed in the injecting device.

In some embodiments of the subject kit, the composition formed by mixing a first HA chain or a derivative thereof coupled to a norbornene moiety or a derivative thereof and a second HA chain or a derivative thereof coupled to a tetrazine moiety or a derivative thereof and a free HA chain, an amino acid, a vitamin, a mineral, an anesthetic, or any combination thereof has a crosslinking degree of 0.01-0.1%, 0.01-0.5%, 0.05-0.1%, 0.1-0.3%, 0.1-0.5%, 0.1-0.75%, 0.1-1%, 1-1.75%, 1-2%, 1-2.5%, 2-2.5%, 2.25-3%, 2.5-3.25%, 3-3.75%, 3.6-4.2%, 4-5.25%, 5-6.5%, 6-7.5%, 7-8.5%, 8-9.25%, 9-10.5%, 10-12.5%, or any range therebetween.

In some embodiments of the subject kit, the composition formed by mixing a first HA chain or a derivative thereof coupled to an unsaturated moiety (e.g. norbornene moiety) or a derivative thereof and a second HA chain or a derivative thereof coupled to a tetrazine moiety or a derivative thereof and a free HA chain, an amino acid, a vitamin, a mineral, an anesthetic, or any combination thereof has a phase angle (δ) of 0.1-0.5°, 0.1-0.9°, 0.5-1°, 0.7-1.5°, 1-2.5°, 2-4.5°, 3-4.75°, 4.7-5.5°, 5-7.5°, 6-8°, 7-8.5°, 8.25-9.5°, 9-10.5°, 9.5-12°, or any range therebetween.

In some embodiments of the subject kit, the composition formed by mixing a first HA chain or a derivative thereof coupled to a norbornene moiety or a derivative thereof and a second HA chain or a derivative thereof coupled to a tetrazine moiety or a derivative thereof and a free HA chain, an amino acid, a vitamin, a mineral, an anesthetic, or any combination thereof has an elastic modulus of 10-500 Pa, 20-1,000 Pa, 30-600 Pa, 40-1,000 Pa, 40-5,000 Pa, 50-10,000 Pa, 500-50,000 Pa, 500-10,000 Pa, 500-5,000 Pa, 500-1,000 Pa, 1,000-50,000 Pa, 1,000-10,000 Pa, 1,000-5,000 Pa, 50-20,000 Pa, 500-20,000 Pa, or 1,000-20,000 Pa, or any range therebetween.

In some embodiments, the components of the kit are packaged within a container.

In some embodiments, the container is made of a material selected from the group consisting of thin-walled film or plastic (transparent or opaque), paperboard-based, foil, rigid plastic, metal (e.g., aluminum), glass, etc.

In some embodiments, the content of the kit is packaged, as described below, to allow for storage of the components until they are needed.

In some embodiments, some or all components of the kit may be packaged in suitable packaging to maintain sterility.

In some embodiments, the packaging has a cap which allows hermetic sealing during storage and which can be pierced by a needle or cannula at the time of use.

In some embodiments, the components of the kit are stored in separate containers within the main kit containment element e.g., box or analogous structure, may or may not be an airtight container, e.g., to further preserve the sterility of some or all of the components of the kit.

In some embodiments, the dosage amount of the first HA chain or a derivative thereof coupled to a norbornene moiety or a derivative thereof, the second HA chain or a derivative thereof coupled to a tetrazine moiety or a derivative thereof, the free HA chain, the amino acid, the vitamin, the mineral, or the anesthetic provided in a kit may be sufficient for a single application or for multiple applications.

In some embodiments, the kit may have multiple dosage amounts of the first HA chain or a derivative thereof coupled to a norbornene moiety or a derivative thereof, the second HA chain or a derivative thereof coupled to a tetrazine moiety or a derivative thereof, the free HA chain, the amino acid, the vitamin, the mineral, or the anesthetic packaged in a single container, e.g., a single tube, bottle, vial, Eppendorf and the like.

In some embodiments, the kit may have multiple dosage amounts of the first HA chain or a derivative thereof coupled to a norbornene moiety or a derivative thereof, the second HA chain or a derivative thereof coupled to a tetrazine moiety or a derivative thereof, the free HA chain, the amino acid, the vitamin, the mineral, or the anesthetic individually packaged such that certain kits may have more than one container of first HA chain or a derivative thereof coupled to a norbornene moiety or a derivative thereof, the second HA chain or a derivative thereof coupled to a tetrazine moiety or a derivative thereof, the free HA chain, the amino acid, the vitamin, the mineral, or the anesthetic.

In some embodiments, multiple dosage amounts of the first HA chain or a derivative thereof coupled to a norbornene moiety or a derivative thereof, the second HA chain or a derivative thereof coupled to a tetrazine moiety or a derivative thereof, the free HA chain, the amino acid, the vitamin, the mineral, or the anesthetic may be packed in single separate containers.

In some embodiments, the kit contains instructions for preparing the composition used therein and for how to practice the methods of the invention.

In some embodiments, the instructions may be recorded on a suitable recording medium or substrate. For example, the instructions may be printed on a substrate, such as paper or plastic, etc.

In some embodiments, the instructions may be present in the kit as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Any concentration ranges, percentage range, or ratio range recited herein are to be understood to include concentrations, percentages or ratios of any integer within that range and fractions thereof, such as one tenth and one hundredth of an integer, unless otherwise indicated.

Any number range recited herein relating to any physical feature, such as polymer subunits, size or thickness, are to be understood to include any integer within the recited range, unless otherwise indicated.

As used herein, the terms "subject" or "individual" or "animal" or "patient" or "mammal," refers to any subject, particularly a mammalian subject, for whom therapy is desired, for example, a human.

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

It should be understood that the terms "a" and "an" as used above and elsewhere herein refer to "one or more" of the enumerated components. It will be clear to one of ordinary skill in the art that the use of the singular includes the plural unless specifically stated otherwise. Therefore, the terms "a" "an" and "at least one" are used interchangeably in this application.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In the description and claims of the present application, each of the verbs, "comprise," "include" and "have" and conjugates thereof, are used to indicate that the object or objects of the verb are not necessarily a complete listing of components, elements or parts of the subject or subjects of the verb.

Other terms as used herein are meant to be defined by their well-known meanings in the art.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

In one embodiment, the term "alkyl" comprises an aliphatic hydrocarbon including straight chain and branched chain groups. Preferably, the alkyl group has 21 to 100 carbon atoms, and more preferably 21-50 carbon atoms. Whenever a numerical range; e.g., "21-100", is stated herein, it implies that the group, in this case the alkyl group, may contain 21 carbon atoms, 22 carbon atoms, 23 carbon atoms, etc., up to and including 100 carbon atoms.

In one embodiment, the term "long alkyl" comprises an alkyl having at least 20 carbon atoms in its main chain (the longest path of continuous covalently attached atoms). A short alkyl therefore has 20 or less main-chain carbons. In one embodiment, an alkyl can be substituted or unsubstituted. In one embodiment, the term "alkyl", as used herein, also encompasses saturated or unsaturated hydrocarbon, hence this term further encompasses alkenyl and alkynyl.

In one embodiment, the term "alkenyl" describes an unsaturated alkyl, as defined herein, having at least two carbon atoms and at least one carbon-carbon double bond. The alkenyl may be substituted or unsubstituted by one or more substituents, as described hereinabove. In one embodiment, the term "alkynyl", as defined herein, is an unsaturated alkyl having at least two carbon atoms and at least one carbon-carbon triple bond. The alkynyl may be substituted or unsubstituted by one or more substituents.

In one embodiment, the term "unsaturated" describes a compound containing one or more unsaturated bond(s). In some embodiments, an unsaturated bond refers to a double bond, and/or to a triple bond.

In one embodiment, the term "cycloalkyl" describes an all-carbon monocyclic or fused ring (i.e., rings which share an adjacent pair of carbon atoms) group where one or more of the rings does not have a completely conjugated pi-electron system. The cycloalkyl group may be substituted or unsubstituted.

In one embodiment, the term "aryl" describes an all-carbon monocyclic or fused-ring polycyclic (i.e., rings which share adjacent pairs of carbon atoms) groups having a completely conjugated pi-electron system. In one embodiment, an aryl group may be substituted or unsubstituted.

In one embodiment, the term alkoxy" describes both an —O-alkyl and an —O-cycloalkyl group. In one embodiment, the term "aryloxy" describes an —O-aryl. In one embodiment, the term alkyl, cycloalkyl and aryl groups in the general formulas herein may be substituted by one or more substituents, whereby each substituent group can independently be, for example, halide, alkyl, alkoxy, cycloalkyl, alkoxy, nitro, amine, hydroxyl, thiol, thioalkoxy, thiohydroxy, carboxy, amide, aryl and aryloxy, depending on the substituted group and its position in the molecule.

In one embodiment, "halide", "halogen" or "halo" describes fluorine, chlorine, bromine or iodine. In one embodiment, "haloalkyl" describes an alkyl group as defined herein, further substituted by one or more halide(s). In one embodiment, "haloalkoxy" describes an alkoxy group as defined herein, further substituted by one or more halide(s). In one embodiment, the term "hydroxyl" or "hydroxy" describes a —OH group. In one embodiment, the term "thiohydroxy" or "thiol" describes a —SH group. In one embodiment, the term "thioalkoxy" describes both an —S-alkyl group, and a —S-cycloalkyl group. In one embodiment, the term "thioaryloxy" describes both an —S-aryl and a —S-heteroaryl group. In one embodiment, the term "amine" describes a —NR'R" group, with R' and R". In one embodiment, the term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine.

In one embodiment, the term "heteroalicyclic" or "heterocyclyl" describes a monocyclic or fused ring group having in the ring(s) one or more atoms such as nitrogen, oxygen and sulfur. The rings may also have one or more double bonds. In one embodiment, the rings do not have a completely conjugated pi-electron system. Representative examples are piperidine, piperazine, tetrahydrofurane, tetrahydropyrane, morpholino and the like.

In one embodiment, the term "carboxy" or "carboxylate" describes a —C(=O)—OR' group, where R' is hydrogen, alkyl, cycloalkyl, alkenyl, aryl, heteroaryl (bonded through a ring carbon) or heteroalicyclic (bonded through a ring carbon).

In one embodiment, the term "carbonyl" describes a —C(=O)—R' group, where R' is as defined hereinabove. In one embodiment, the above-terms also encompass thio-derivatives thereof (thiocarboxy and thiocarbonyl).

In one embodiment, the term "thiocarbonyl" describes a —C(=S)—R' group, where R' is as defined hereinabove. In one embodiment, the term "thiocarboxy" group describes a —C(=S)—OR' group, where R' is as defined herein. In one embodiment, the term "sulfinyl" group describes an —S(=O)—R' group, where R' is as defined herein. In one embodiment, the term sulfonyl" or "sulfonate" group describes an —S(=O)2-R' group, where R' is as defined herein. In one embodiment, the term "carbamyl" or "carbamate" group describes an —OC(=O)—NR'R" group, where R' is as defined herein and R" is as defined for R'.

In one embodiment, the term "nitro" group refers to a —NO2 group. In one embodiment, the term "cyano" or "nitrile" group refers to a refers to a —N3 group. In one embodiment, the term "sulfonamide" refers to a —S(=O) 2-NR'R" group, with R' and R" as defined herein." refers to a —N3 group. In one embodiment, the term "sulfonamide" refers to a —S(=O)2-NR'R" group, with R' and R" as defined herein.

In one embodiment, the term "phosphonyl" or "phosphonate" describes an —O—P(=O)(OR')2 group, with R' as defined hereinabove. In one embodiment, the term "phosphinyl" describes a —PR'R" group, with R' and R" as defined hereinabove.

In one embodiment, the term "alkaryl" describes an alkyl, as defined herein, which substituted by an aryl or a heteroaryl, as described herein. In one embodiment, alkaryl is benzyl.

In one embodiment, the term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted by one or more substituents, as described hereinabove. Representative examples are thiadiazole, pyridine, pyrrole, oxazole, indole, purine and the like.

In one embodiment, the terms "halo" and "halide", which are referred to herein interchangeably, describe an atom of a halogen, that is fluorine, chlorine, bromine or iodine, also referred to herein as fluoride, chloride, bromide and iodide. In one embodiment, the term "haloalkyl" describes an alkyl group as defined above, further substituted by one or more halide(s).

EXAMPLES

Materials and Methods
Method A: Preparation of HA-tetrazine or HA-norbornene
Hyaluronic acid sodium salt was dissolved at a concentration of 5 to 10 mg/g in 2-(N-morpholino) ethanesulfonic acid (MES) buffer (100 mM, pH 5.5). After obtaining a homogeneous solution, 4-(4,6-dimethoxy-1,3,5-triazin-2-yl)-4-methyl-morpholinium chloride (DMTMM) was added followed by the primary amine to be coupled. The amounts of reagents were adjusted according to desired degree of modification. The reaction was left under agitation at 10 to 50° C. for 24 hours, then dialyzed (MWCO=12 kDa) against a saturated solution of NaCl for 24 hours, and then several times against purified water. The solution was transferred to a flask, chilled to −80° C. and frozen dried to provide the modified HA product under solid form.

Method B: Preparation of HA-Tetrazine or HA-Norbornene or HA-Styrene
Hyaluronic acid sodium salt was dissolved at a concentration of 5 to 10 mg/g in double distilled water (DDW). After obtaining a homogeneous solution, 4-(4,6-dimethoxy-1,3,5-triazin-2-yl)-4-methyl-morpholinium chloride (DMTMM) was added followed by the primary amine to be coupled. The amounts of reagents were adjusted according to desired degree of modification. The reaction was left under agitation at 20 to 90° C. for 4 hours, then dialyzed (MWCO=12 kDa) against a saturated solution of NaCl for 24 hours, and then several times against purified water. The solution was transferred to a flask, chilled to −80° C. and frozen dried to provide the modified HA product under solid form.

Determination of the Modification Degrees of HA-Tetrazine, HA-Norbornene, HA-Styrene and the Crosslinking Degree of the Gel For determination of the modification degree, the dry sample of modified HA (e.g. HA-tetrazine or HA-norbornene or HA-styrene) was solubilized in D$_2$O and treated with hyaluronidase (from bovine testes, Type IV-S from Sigma Aldrich) at a final concentration of 300 units/mL until the solution was liquid. The sample was analyzed by $^1$H NMR. Modification degree was determined by calculating the integration ratios as described herein below.

Modification degree of HA-tetrazine (formula IIIB) the ratio between the area under the peaks corresponding to aromatic protons of tetrazine (at 7.5 to 7.7 ppm and 8.1 to 8.9 ppm, 8H) and the area under the peak corresponding to N-acetyl proton of glucosamine residue of hyaluronic acid (at 2.0 ppm, 3H) is calculated. The $^1$H NMR spectrum of HA-tetrazine is provided in FIG. 1.

Figure 2:
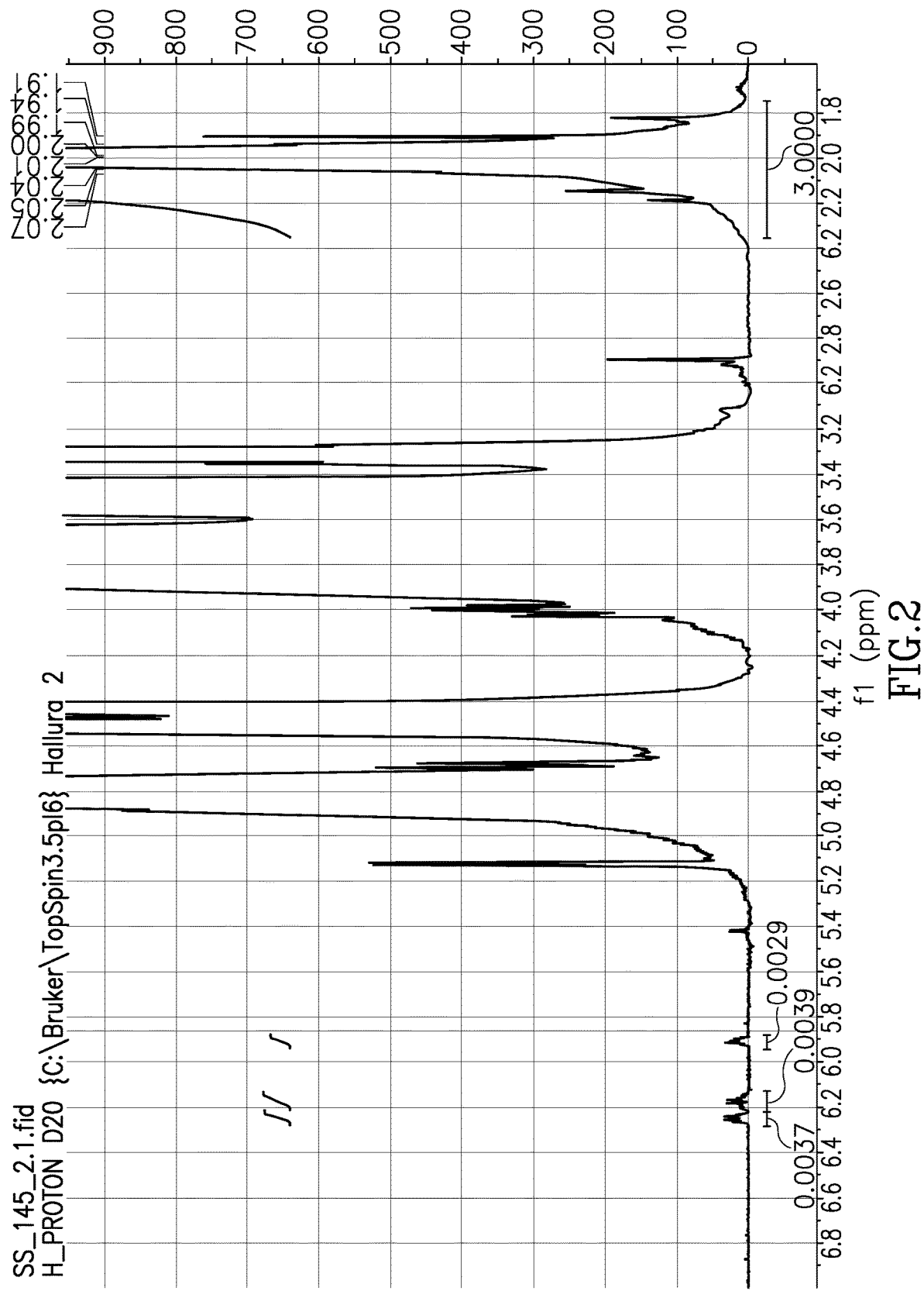
FIG. 2: An $^1$H NMR spectrum of hyaluronic acid modified with norbornene (HA-norbornene), showing alkene peaks of norbornene, and an aliphatic peak of the N-acetyl glucosamine residue.

Modification degree of HA-norbornene (formula IIA) the ratio between the area under the peaks corresponding to alkene protons (at 5.8 to 6.3 ppm, 2H) and the area under the peak corresponding to N-acetyl proton of glucosamine residue of hyaluronic acid (at 2.0 ppm, 3H). The $^1$H NMR spectrum of HA-norbornene is provided in FIG. 2.

Figure 3:
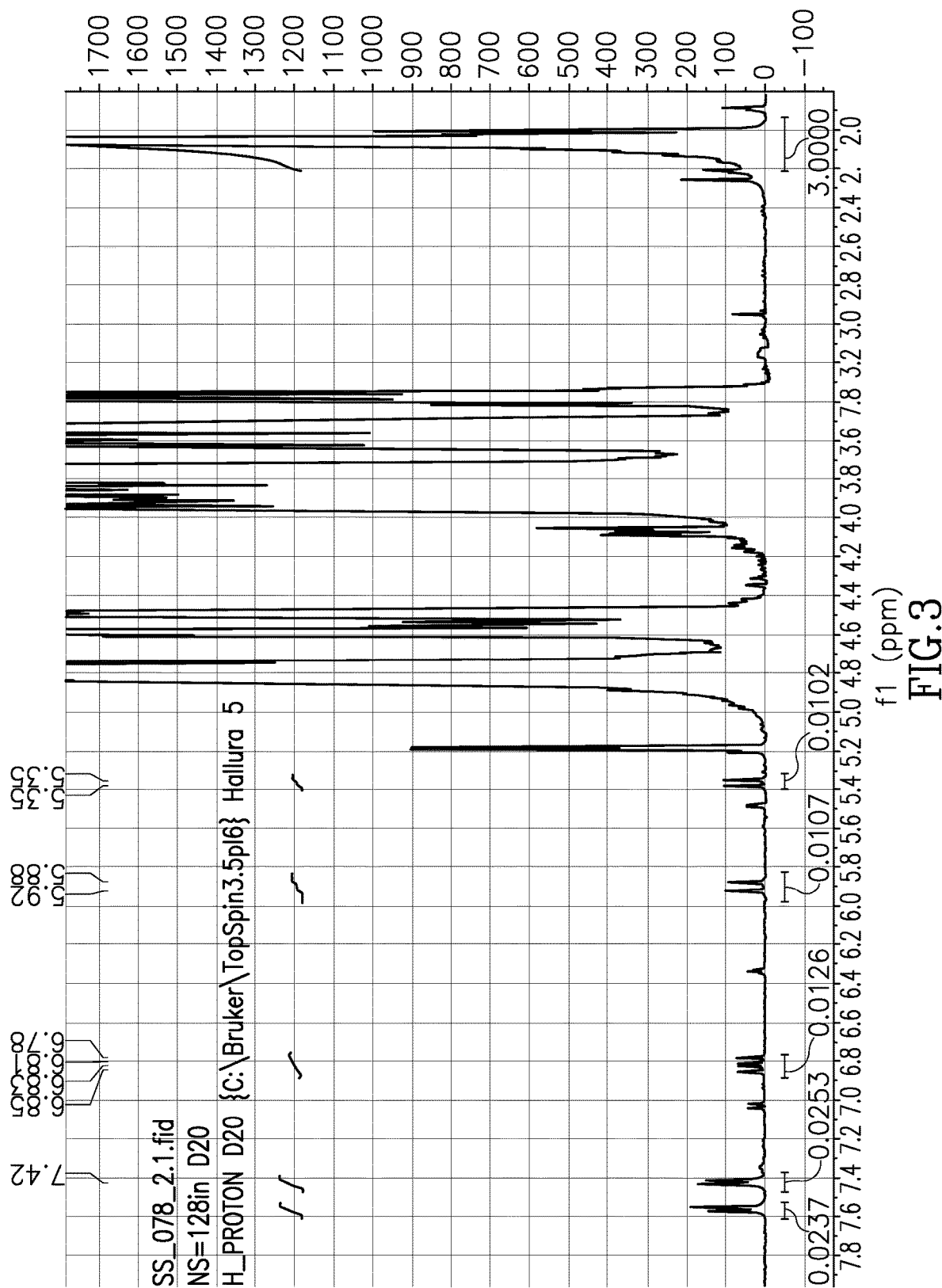
FIG. 3: An $^1$H NMR spectrum of hyaluronic acid modified with styrene (HA-styrene), showing alkene peaks of styrene, and an aliphatic peak of the N-acetyl glucosamine residue.

Modification degree of HA-styrene (formula IA): the ratio between the area under the peaks corresponding to alkene protons (at 5.36 ppm, 5.90 ppm and 6.8 ppm, 3H), and the area under the signal corresponding to N-acetyl proton of glucosamine residue of hyaluronic acid (at 2.0 ppm, 3H). The $^1$H NMR spectrum of HA-styrene is provided in FIG. 3.

The crosslinking degree of the gel is calculated according to the following equation:

$$D_c = \frac{\frac{D_m(Tet)}{M(Tet)} + \frac{D_m(Nor)}{M(Nor)}}{M(Tet) + M(Nor)}$$

[$D_c$=($D_m$(Tet)/M(Tet)+$D_m$(Nor)/M(Nor))/(M(Tet)+M(Nor))]

wherein:
$D_c$ is the cross-linking degree of the gel;
$D_m$ (Tet) is the modification degree of HA-tetrazine, determined by $^1$H NMR;
$D_m$ (Nor) is the modification degree of HA-norbornene, determined by $^1$H NMR,
M(Tet) is the weight of HA-tetrazine engaged in the crosslinking,
M(Nor) is the weight of HA-norbornene engaged in the crosslinking.

Cross-Linking of HA-Tetrazine and HA-Norbornene

Two samples of HA-tetrazine and HA-norbornene were separately dissolved in a phosphate buffer solution at the pH value ranging from 6.8 to 7.8 and at the concentration specified herein below (Table 1). The same volume of the two solutions were mixed and left under agitation at 37° C. for 18 hours and then further at room temperature until the rheological gel parameters were stable. For samples including non-crosslinked hyaluronic acid, a solution at the same concentration of non-crosslinked hyaluronic acid was added after reaction and homogenized under agitation. The cross-linking degree of the obtained gel was the mean of the modification degrees of the HA-tetrazine and HA-norbornene used.

Measurement of the Rheological Parameters

Measurements of the phase angle δ (in °) and the elastic modulus G' (in Pa) were performed at 25° C., at a frequency of 1 Hz with a stress sweep from 1 to 1,000 Pa or a strain sweep of 0.35 to 3500%, using a rheometer (Thermo Haake MARS 6000 or RS1 or TA DHR1) with a serrated or sandblasted plate-plate geometry of 20 mm diameter.

TABLE 1

Summary of rheological tests

| Ent. | Product name if commercially available | HA (mg/gr) | Non-crosslinked HA content | Linker | Crosslinking degree | G' (Pa) | δ (°) |
|---|---|---|---|---|---|---|---|
| 1 | Restylane | 20 mg/gr | unknown | BDDE | 1% | 705 | 9.8 |
| 2 | Restylane Defyne (Emervel Deep) | 20 mg/gr | unknown | BDDE | 9% | 254 | 5.4 |
| 3 | Juvederm Voluma | 20 mg/gr | unknown | BDDE | 6% | 298 | 5.6 |
| 4 | Juvederm Volift | 17.5 mg/gr | unknown | BDDE | 6% | 218 | 8.1 |
| 5 | Juvederm Volbella | 15 mg/gr | unknown | BDDE | 6% | 181 | 10 |
| 6 | Juvederm Ultra 2 | 24 mg/gr | unknown | BDDE | 5% | 260 | 15.8 |
| 7 |  | 10 mg/gr | 0 | IIA/IIIB | 3.5% | 558 | 0.78 |
| 8 |  | 10 mg/gr | 10% | IIA/IIIB | 1.3% | 178 | 4.6 |
| 9 |  | 10 mg/gr | 10% | IIA/IIIB | 1.1% | 181 | 3.5 |
| 10 |  | 10 mg/gr | 0 | IIA/IIIB | 0.35% | NA liquid product | NA liquid product |
| 11 |  | 10 mg/gr | 0 | IIA/IIIB | 1.1% | 260 | 1.9 |
| 12 |  | 10 mg/gr | 5% | IIA/IIIB | 1.1% | 238 | 2.4 |
| 13 |  | 10 mg/gr | 10% | IIA/IIIB | 1.1% | 181 | 3.5 |
| 14 |  | 10 mg/gr | 20% | IIA/IIIB | 1.1% | 195 | 4.3 |
| 15 |  | 15 mg/gr | 10% | IIA/IIIB | 1.3% | 387 | 4 |
| 16 |  | 10 mg/gr | 10% | IIA/IIIB | 1.3% | 178 | 4.6 |
| 17 |  | 5 mg/gr | 10% | IIA/IIIB | 1.3% | 54 | 4.3 |
| 18 |  | 10 mg/gr | 10% | IIF/IIIB | 0.25% | 88 | 6.1 |
| 19 |  | 10 mg/gr | 10% | IIA/IIIA | 3.5% | 350 | 6.3 |
| 20 |  | 10 mg/gr | 0 | IIA/IIIB | 0.9% | 74 | 1.3 |

TABLE 1-continued

Summary of rheological tests

| Ent. | Product name if commercially available | HA (mg/gr) | Non-crosslinked HA content | Linker | Crosslinking degree | G' (Pa) | δ (°) |
|---|---|---|---|---|---|---|---|
| 21 | | 7.5 mg/gr | 0 | IIA/IIIB | 0.9% | 34 | 3.8 |
| 22 | | 5 mg/gr | 0 | IIA/IIIB | 0.9% | 13 | 5.2 |
| 23 | | 10 mg/gr | 0 | IA/IIIB | 1.1% | 73 | 3.1 |
| 24 | | 7.5 mg/gr | 0 | IA/IIIB | 1.1% | 44 | 5.5 |
| 25 | Juvederm Volite | 12 mg/gr | unknown | BDDE | 6% | 118 | 15.1 |
| 26 | Restylane Skin Booster | 12 mg/gr | unknown | BDDE | 1% | 43 | 38.4 |

Linkers used in entries 7-24 are presented e.g., in claims 5, and 7 herein below.

Example 1

Rheological Parameters of HA-Crosslinked Polymers

First, commercially available dermal fillers were examined (Table 1, Entries 1-6, 25, 26). Data showed that δ smaller than 10° were obtained only in commercial products with high content in HA (20 mg/gr—Entries 1-3) and/or high crosslinking degrees (6-9%—Entries 2-5). A product with both high content in HA and high crosslinking degree leading to δ greater than 10° was also observed (Entry 6). Products with lower concentrations (12 mg/gr, Entries 25-26) and with high or low crosslinking degrees (6%—Entry 25 or 1%—Entry 26) led to δ greater than 10°.

The samples containing 10 mg/gr of hyaluronic acid were formulated with various crosslinking degrees (Table 1, Entries 7-10, 20). Low δ were obtained for crosslinking degrees ranging from 3.5% to 0.9%. However, very low crosslinking degrees, such as 0.35% failed to lead to the formation of a gel (Entry 10).

Samples were then formulated with 10 mg/gr of hyaluronic acid with different contents of non-crosslinked HA added to the final product (Table 1, Entry 11-14). The addition of non-crosslinked HA reduced the lifting capacity of the crosslinked material, as was observed by the increase in δ value. Nonetheless, gels comprising HA contents of up to 20% still demonstrated δ values below 10°.

Samples formulated with a fixed crosslinking degree were further formulated at 1.3% or 0.9% and various contents of HA (Table 1, Entry 15-17, 20-22). The reduction from 15 mg/gr to 10 mg/gr and 5 mg/gr (Entry 15-17) or from 10 mg/gr to 7.5 mg/gr and 5 mg/gr (Entry 20-22) reduced the gel elastic modulus (G') of the crosslinked material. However, even for a HA content as low as 5 mg/gr, the δ value remained under 10°.

To test the generality of the cross-linking molecules, tetrazine derivatives and norbornene derivatives were mixed with fixed HA content (10 mg/gr; Table 1, Entry 18-19). As demonstrated, δ values below 10° were obtained.

To test the substitution of norbornene by another unsaturated moiety, HA was modified by styrene (formula IA). A tetrazine derivative was mixed with the styrene derivative at a crosslinking degree of 1.1% and a HA content of 10 mg/gr or 7.5 mg/gr providing δ values below 10° (Table 1, Entry 23-24).

Figure 4:
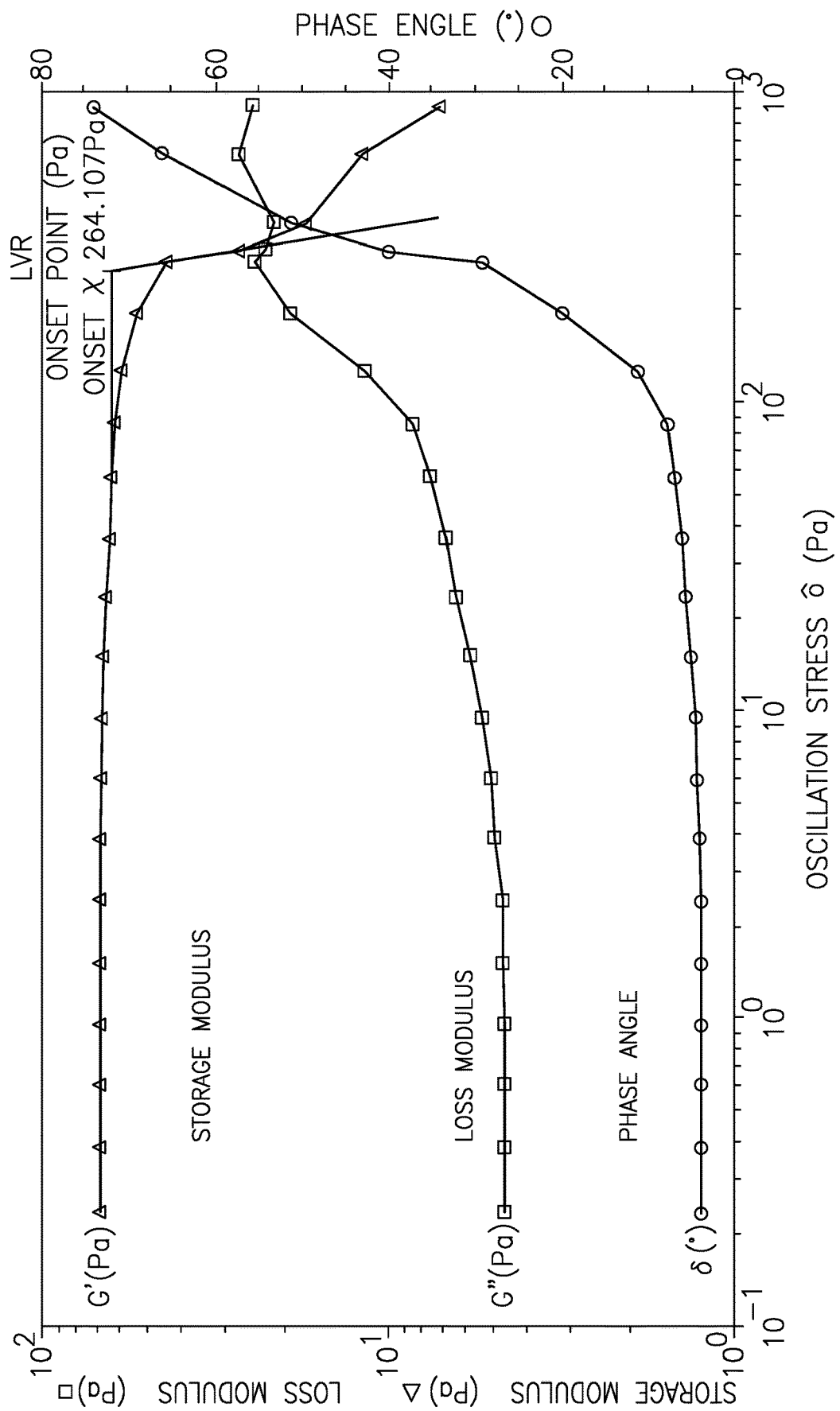
FIG. 4: A graph depicting the onset point of a polymer in the linear viscoelastic region (LVR).

The Linear viscoelastic region (LVR) represents a linear region of the elastic modulus (G') under dynamic strain/stress sweep. Longer LVR region is related to superior characteristic of the gel, as it retains its viscoelastic properties with increasing levels of the applied forces. The LVR was measured as on onset point (a crossover of 2 tangents of the G' curve) in standard strain sweep cycle of the rheometer (TA DHR1), as exemplified by FIG. 4.

Commercial dermal fillers provided a range of onset values, from very low as 9.4 Pa (Table 2, Entry 7) to very high as 421 Pa (Table 2, Entry 2). LVR data for commercial products clearly show a correlation with the content in HA (Table 2, Entries 3-6 at 6% of crosslinking degree, Entries 1 and 7 at 1% of crosslinking degree). LVR data for commercial products also show a clear correlation with the crosslinking degree (Table 2, Entry 1-3 at 20 mg/gr). Gels according to the invention show similar correlation between LVR and HA content and crosslinking degree (Table 2, Entry 8-13). However, gels according to the invention show higher LVR, and thus superior characteristics of the material, than commercial products while including lower HA content and lower crosslinking degrees (Table 2, Entry 8-12 versus Entry 1,4-7, and Entry 13 versus Entry 7).

TABLE 2

Comparison of LVR values

| Ent. | Product name available | HA (mg/gr) | Non-crosslinked HA content | Linker | Crosslinking degree | LVR Onset point (Pa) |
|---|---|---|---|---|---|---|
| 1 | Restylane | 20 | unknown | BDDE | 1% | 28 |
| 2 | Restylane Defyne (Emervel Deep) | 20 | unknown | BDDE | 9% | 421 |
| 3 | Juvederm Voluma | 20 | unknown | BDDE | 6% | 257 |
| 4 | Juvederm Volift | 17.5 | unknown | BDDE | 6% | 89 |
| 5 | Juvederm Volbella | 15 | unknown | BDDE | 6% | 59.1 |
| 6 | Juvederm Volite | 12 | unknown | BDDE | 6% | 26.2 |
| 7 | Restylane Skin Booster | 12 | unknown | BDDE | 1% | 9.4 |

TABLE 2-continued

Comparison of LVR values

| Ent. | Product name available | HA (mg/gr) | Non-crosslinked HA content | Linker | Crosslinking degree | LVR Onset point (Pa) |
|---|---|---|---|---|---|---|
| 8  |  | 10      | 0 | IIA/IIIB | 0.9% | 263  |
| 9  |  | 7.5     | 0 | IIA/IIIB | 0.9% | 132  |
| 10 |  | 5       | 0 | IIA/IIIB | 0.9% | 103  |
| 11 |  | 10      | 0 | IIA/IIIB | 0.6% | 154  |
| 12 |  | 7.5     | 0 | IIA/IIIB | 0.6% | 100.5 |
| 13 |  | 5 mg/gr | 0 | IIA/IIIB | 0.6% | 23.6 |

Example 2

Extrudability of HA-Crosslinked Polymers

Two samples of HA-tetrazine and HA-norbornene were separately dissolved in a phosphate buffer solution at pH 7.0 at the same concentration. Subsequently, the same volume of each sample were mixed together and immediately introduced to 1 mL long Cyclo Olefin Polymer (COP) syringes. All syringes were incubated at 37° C. for 18 hours. And then further at room temperature until the rheological gel parameters were stable.

Extrusion force was measured using a Mecmesin traction bench instrument. The data was acquired by extrusion of gel from 1 mL syringe equipped with 27 G ½" or 29½" or 30 G ½" needles at a standard rate of 12.5 mm/min. For gels prepared as described herein above, no sieving or fragmentation was performed.

Representative extrusion force data is presented in Table 3. Restylane and Voluma are offered with 29 G ½" and 27 G ½" needles respectively (Table 3, entries 1-2), and have relatively high G' values (Table 1, Entry 1, 3). Volbella is offered with 30 G ½" needles (Table 3, Entry 3), with mid-range G' (Table 1, Entry 5).

Entry. 4-9 in Table 3, represent gels of the invention, which were prepared inside the 1 mL syringe without sieving or homogenization. As shown in Table 3, the extrusion force values are within the acceptable range. Gel in Entry 4 was extruded via 27 G ½" needles, while gels from Entry 5-9 were extruded via 30 G ½" needles.

TABLE 3

Extrusion force values

| Ent. | Product name if commercially available | HA (mg/gr) | Non-crosslinked HA content | Linker | Crosslinking degree | Extrusion force (Pa) |
|---|---|---|---|---|---|---|
| 1 | Restylane         | 20 mg/gr  | unknown | BDDE     | 1%   | 12.6 |
| 2 | Juvederm Voluma   | 20 mg/gr  | unknown | BDDE     | 6%   | 8.0  |
| 3 | Juvederm Volbella | 15 mg/gr  | unknown | BDDE     | 6%   | 6.8  |
| 4 |                   | 10 mg/gr  | 0       | IIA/IIIB | 0.9% | 18.5 |
| 5 |                   | 7.5 mg/gr | 0       | IIA/IIIB | 0.9% | 25.5 |
| 6 |                   | 5 mg/gr   | 0       | IIA/IIIB | 0.9% | 15.7 |
| 7 |                   | 10 mg/gr  | 0       | IIA/IIIB | 0.5% | 18.7 |
| 8 |                   | 7.5 mg/gr | 0       | IIA/IIIB | 0.5% | 13.5 |
| 9 |                   | 5 mg/gr   | 0       | IIA/IIIB | 0.5% | 3.5  |

Example 3

Gel Swelling in Water

Gel samples were prepared by mixing 200 mg of each product with DDW (1.0 ml) and incubating for 6 hours at 37° C. After centrifugation of the mixture (twice at 10,000 rpm for 10 min), the water supernatant was carefully withdrawn, and the remaining swollen gel was weighted. The swelling ratio was calculated by following equation:

Swelling ratio=(weight of the swollen gel)/(initial weight of the gel).

TABLE 4

Gel swelling ratios in water

| Ent. | Product name if commercially available | HA (mg/gr) | Non-crosslinked HA content | Linker | Crosslinking degree | Gel swelling ratio |
|---|---|---|---|---|---|---|
| 1 | Restylane | 20 mg/gr | unknown | BDDE | 1% | 3.4 |
| 2 | Juvederm Voluma | 20 mg/gr | unknown | BDDE | 6% | 4.0 |
| 3 | Juvederm Volbella | 15 mg/gr | unknown | BDDE | 6% | 3.2 |
| 4 | | 10 mg/gr | 0 | IIA/IIIB | 0.9% | 2.4 |
| 5 | | 7.5 mg/gr | 0 | IIA/IIIB | 0.9% | 1.9 |
| 6 | | 5 mg/gr | 0 | IIA/IIIB | 0.9% | 2.2 |

Results show lower gel swelling ratios for the gels prepared according to the invention (Table 4, Entries 4-6) as compared to commercially available dermal fillers with higher content in HA and/or higher crosslinking degrees (Table 4, Entry 1-3). Reduction of the gel swelling in water is likely to reduce the risk of swelling and edema in vivo.

Example 4

In Vivo Implantation Data

Five Sprague-Dawley rats were injected subcutaneously by gel samples (corresponding to Table 4, Entry 1, 2, 4-6) using 27 G ½" hypodermic needles. Each animal received 5 injections of 100 microliters of gel samples on day 1. Each gel sample was injected 5 times in various animals. Animals were followed for 95 days post injection. No erythema nor edema were found in any animals at any of the injected sites. No change in general health in any of the animals were found during the study period. Histopathologic evaluation of the injected sites after 95 days post injection did not reveal pathological changes in any of the injected sites.

Figure 5:
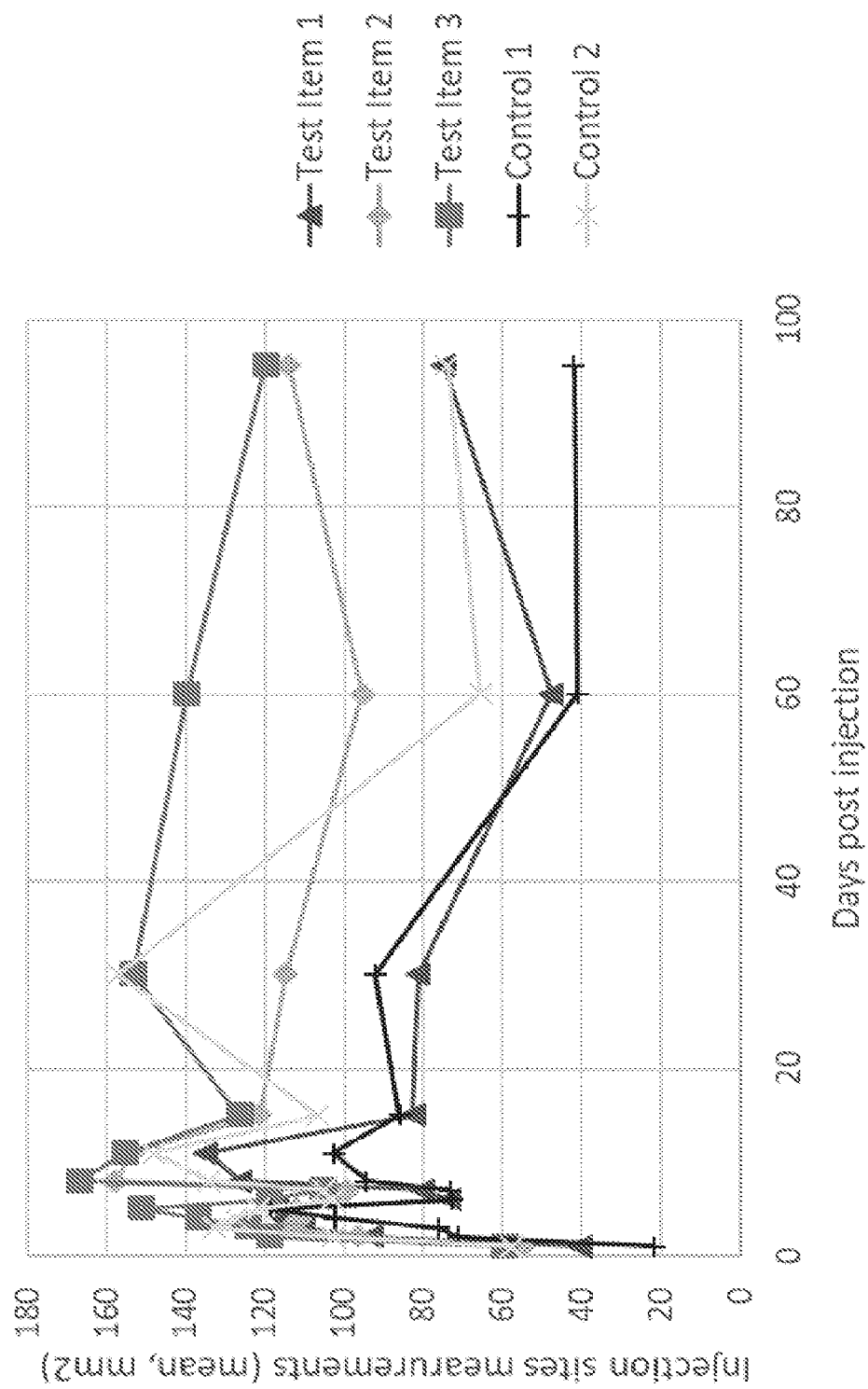
FIG. 5: A graph depicting the size of a subcutaneous gel matter during 95-day period after in-vivo administration of commercial products vs. polymers of the invention.

During the course of the study from day 1 to day 95 post injection, the size of the subcutaneous gel mass was measured with an electronic caliper. The size of the gel subcutaneously was calculated as the length by the width of the bolus detected under the skin by palpation and measured with an electronic caliper. The average data for the 5 injected sites per products (FIG. 5) shows a significant larger size of gel mass for Test Item 2 (gel described in Table 4, Entry. 5) and Test Item 3 (gel described in Table 4, Entry 4) than the two controls which are commercially available dermal fillers with higher content in HA and/or higher crosslinking degrees (Control 1 is described in Table 4, Entry 2, Control 2 is described in Table 2, Entry 1). Test Item 1 (gel described in Table 4, Entry 6) with a very low HA content of 5 mg/gr show the same size of gel bolus subcutaneously as Control 2 which has a much higher HA content of 20 mg/gr (gel described in Table 4, Entry 1).

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A polymer comprising a first hyaluronic acid (HA) chain and a second HA chain, wherein said first HA chain and said second HA chain are crosslinked via one or more linkers, wherein said one or more linkers are represented by formula (C):

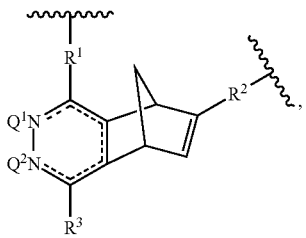

or by formula (D):

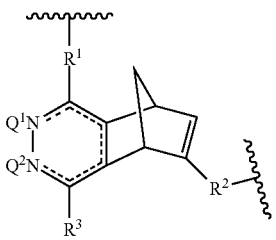

or a combination thereof; wherein:
- - - represents a single or a double bond;
$R^1$ is selected from the group consisting of: a bond, alkyl, alkenyl, cycloalkyl, aryl, heteroaryl, heteroalicyclic, C(O)—NH-alkyl-NH, and —$C_0$-$C_6$alkyl-ZN— wherein Z is a bond, aryl, or heteroaryl, wherein said aryl or said heteroaryl is optionally substituted with halogen, hydroxy, $C_1$-$C_6$alkyl, $C_1$-$C_6$alkoxy, ($C_1$-$C_6$alkyl) amino, and di($C_1$-$C_6$alkyl)amino;

$R^2$ is C(O)—NH-alkyl-NH;

$Q^1$, $Q^2$ or both represent hydrogen, or are absent;

$R^3$ is selected from the group consisting of: hydrogen, alkyl, aryl, or heteroaryl substituted or non-substituted, and wherein said polymer is characterized by a cross-linking degree of 0.2 to 4% and wherein said polymer is characterized by at least one of: a phase angle (δ) of 0.1 to 10°, an elastic modulus (G') of 10 to 1,000 Pa.

2. The polymer of claim 1, wherein R1 is selected from an aryl or a heteroaryl optionally substituted with any one of: $C_1$-$C_6$alkyl, $C_1$-$C_6$alkoxy, ($C_1$-$C_6$alkyl) amino, and di($C_1$-$C_6$alkyl)amino.

3. The polymer of claim 1, wherein said R3 is selected from an aryl and a heteroaryl substituted or non-substituted.

4. The polymer of claim 1, wherein said crosslinking degree is identical with an average modification degree of (i) the first HA chain and (ii) the second HA chain; and wherein said modification degree is determined by $^1$H NMR.

5. The polymer of claim 3, wherein said linker is represented by formula:

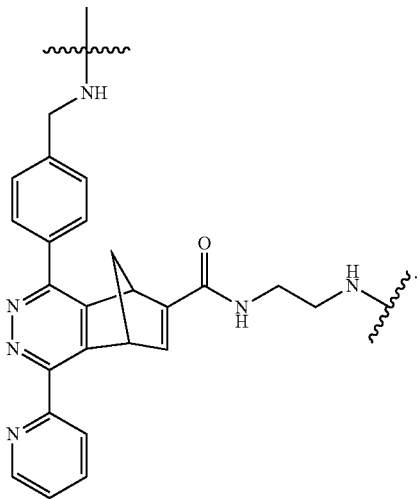 [SMILES: *NCCNC(=O)C1=CC2CC1c1c(-c3ccc(CN*)cc3)nnc(-c3ccccn3)c12]

6. A composition comprising the polymer of claim 1 and a pharmaceutically acceptable carrier, wherein the composition is an injectable gel; and wherein said composition is characterized by at least one of: a phase angle (δ) of 0.1 to 10°; an elastic modulus (G') of 10 to 1,000 Pa; LVR onset point above 28 Pa; and swelling ratio below 3.

7. The composition of claim 6, and wherein a w/w concentration of said polymer within the composition is between 0.1 and 1.9%.

8. The composition of claim 6, further comprising 0.1-30% (w/w) non-cross-linked HA, of the total HA content in said composition.

9. The composition of claim 6,
wherein the composition is an injectable a gel; and wherein said composition is characterized by a phase angle (δ) of 0.1 to 10°; an elastic modulus (G') of 10 to 1,000 Pa; LVR onset point above 28 Pa; and swelling ratio below 3; and wherein a w/w concentration of said polymer within the composition is between 0.1 and 1%.

10. A method for filling or volumizing a tissue in a subject in need thereof, comprising administering the polymer of claim 1 to said tissue, thereby filling or volumizing a tissue in a subject in need thereof.

11. The method of claim 10, wherein said tissue is selected from the group consisting of: skin, gingival, cartilage and ophthalmic tissue, muscles, and subcutaneous tissues.

12. A method for filling or volumizing a tissue in a subject in need thereof, comprising administering the composition of claim 6 to said tissue, thereby filling or volumizing a tissue in a subject in need thereof.

13. A process for preparing the polymer of claim 1, the process comprising: mixing a first hyaluronic acid (HA) chain and a second HA chain, wherein said first HA chain comprises an unsaturated moiety or a derivative thereof and said second HA chain comprises a tetrazine moiety or derivative thereof, wherein said unsaturated moiety or a derivative thereof and said tetrazine moiety or a derivative thereof are present in a molar ratio of 3:1 to 1:3; thereby crosslinking said first HA chain to said second HA chain.

14. The process of claim 13, wherein said unsaturated moiety comprises a norbornene moiety or a derivative thereof.

15. The process of any one of claim 13, wherein said crosslinking comprises forming a covalent bond between said norbornene moiety or a derivative thereof and said tetrazine moiety or a derivative thereof.

\* \* \* \* \*